US008580254B2

(12) United States Patent
Adam et al.

(10) Patent No.: US 8,580,254 B2
(45) Date of Patent: Nov. 12, 2013

(54) ANTI-IGF ANTIBODIES

(75) Inventors: Paul Adam, Vienna (AT); Elinborg Ostermann, Vienna (AT)

(73) Assignee: Boehringer Ingelheim International GmbH, Ingelheim am Rhein (DE)

(*) Notice: Subject to any disclaimer, the term of this patent is extended or adjusted under 35 U.S.C. 154(b) by 305 days.

(21) Appl. No.: 12/665,373

(22) PCT Filed: Jun. 19, 2008

(86) PCT No.: PCT/EP2008/057789
§ 371 (c)(1),
(2), (4) Date: Mar. 31, 2010

(87) PCT Pub. No.: WO2008/155387
PCT Pub. Date: Dec. 24, 2008

(65) Prior Publication Data
US 2010/0196395 A1    Aug. 5, 2010

(30) Foreign Application Priority Data
Jun. 19, 2007  (EP) .................................... 07110587

(51) Int. Cl.
*A61K 39/395* (2006.01)
*C07K 16/22* (2006.01)

(52) U.S. Cl.
USPC ................. 424/130.1; 530/387.1; 530/388.1; 530/388.24; 424/141.1; 424/145.1

(58) Field of Classification Search
None
See application file for complete search history.

(56) References Cited

U.S. PATENT DOCUMENTS

| 3,773,919 A | 11/1973 | Boswell et al. |
| 4,342,566 A | 8/1982 | Theofilopoulos et al. |
| 6,342,221 B1 * | 1/2002 | Thorpe et al. ............. 424/178.1 |
| 6,696,245 B2 | 2/2004 | Winter et al. |
| 6,991,790 B1 | 1/2006 | Lam et al. |
| 7,020,563 B1 | 3/2006 | Bentley et al. |
| 7,037,498 B2 | 5/2006 | Cohen et al. |
| 7,060,268 B2 | 6/2006 | Andya et al. |
| 7,438,911 B2 | 10/2008 | Shitara et al. |
| 7,498,415 B2 | 3/2009 | Shitara et al. |
| 7,749,966 B2 | 7/2010 | Raso |
| 8,318,159 B2 | 11/2012 | Adam et al. |
| 2006/0165695 A1 | 7/2006 | Shitara et al. |
| 2007/0196376 A1 | 8/2007 | Raeber et al. |
| 2009/0016967 A1 | 1/2009 | Schnapp et al. |
| 2010/0099147 A1 | 4/2010 | Hariharan et al. |
| 2010/0150940 A1 | 6/2010 | Adam et al. |

FOREIGN PATENT DOCUMENTS

| CA | 2473039 A1 | 7/2003 |
| CA | 2483848 A1 | 11/2003 |
| CA | 2536288 A1 | 3/2005 |
| CA | 2540133 A1 | 3/2005 |
| CA | 2540138 A1 | 3/2005 |
| EP | 0123228 A2 | 10/1984 |
| EP | 0292656 A1 | 11/1988 |
| EP | 0492552 A1 | 7/1992 |
| EP | 0700994 A1 | 3/1996 |
| EP | 1505075 A1 | 2/2005 |
| JP | 2003310275 A | 11/2003 |
| WO | 8500831 A1 | 2/1985 |
| WO | 8911297 A1 | 11/1989 |
| WO | 9000562 A1 | 1/1990 |
| WO | 9429348 A2 | 12/1994 |
| WO | 9525794 A1 | 9/1995 |
| WO | 9928347 A1 | 6/1999 |
| WO | 02053596 A2 | 7/2002 |
| WO | 02056910 A1 | 7/2002 |
| WO | 03002609 A2 | 1/2003 |
| WO | 03050531 A2 | 6/2003 |
| WO | 03059951 A2 | 7/2003 |
| WO | 03093317 A1 | 11/2003 |
| WO | 03100008 A2 | 12/2003 |
| WO | 03106621 A2 | 12/2003 |
| WO | 2004003019 A2 | 1/2004 |
| WO | 2004058821 A2 | 7/2004 |
| WO | 2004071529 A2 | 8/2004 |
| WO | 2004083248 A1 | 9/2004 |
| WO | 2005005635 A2 | 1/2005 |
| WO | 2005016970 A2 | 2/2005 |
| WO | 2005018671 A1 | 3/2005 |
| WO | 2005027970 A1 | 3/2005 |
| WO | 2005028515 A1 | 3/2005 |
| WO | 2005058967 A2 | 6/2005 |
| WO | 2005061541 A1 | 7/2005 |

(Continued)

OTHER PUBLICATIONS

Green. Antibody engineering via genetic engineering of the mouse: XenoMouse strains are a vehicle for the facile generation of therapeutic human monoclonal antibodies. Journal of Immunological Methods, 1999. vol. 231. pp. 11-23.*
Rudikoff, Giusti, Cook, and Scharff. Single amino acid substitution altering antigen binding specificity. Proceedings of the National Academy of Science, 1982. vol. 79, p. 1979.*
Mac Callum, Martin, and Thornton. Antibody-antigen interactions: contact analysis and binding site topography. Journal of Molecular Biology, 1996. vol. 262, pp. 732-745.*
De Pascalis, Iwahashi, Tamura, Padlan, Gonzales, Santos, Giuliano, Schuck, Schlom, and Kashmiri. Grafting of abbreviated complementarity determining regions containing specificity determining residues essential for ligand contact to engineer a less immunogenic humanized monoclonal antibody. Journal of Immunology, 2002. vol. 169, pp. 3076-3084.*

(Continued)

*Primary Examiner* — Marianne P Allen
(74) *Attorney, Agent, or Firm* — Michael P. Morris; Edouard G. Lebel

(57) ABSTRACT

Antibody molecules, in particular fully human antibodies that bind to human IGF-1 and cross-react with IGF-2 such that binding of IGF-1 and IGF-2 to the IGF-1 receptor is prevented and IGF-1 receptor-mediated signaling is inhibited. The antibodies do not bind to insulin and thus do not affect the mitogenic properties of insulin that are mediated by its binding to the insulin receptors. The antibodies are useful for the treatment of hyperproliferative diseases, in particular cancer.

17 Claims, 20 Drawing Sheets

(56) References Cited

FOREIGN PATENT DOCUMENTS

| WO | 2006008639 A1 | 1/2006 |
|---|---|---|
| WO | 2006069202 A2 | 6/2006 |
| WO | 2006/125640 A2 | 11/2006 |
| WO | 2007012614 A2 | 2/2007 |
| WO | 2007042309 A2 | 4/2007 |
| WO | 2007070432 A2 | 6/2007 |
| WO | 2007115814 A2 | 10/2007 |
| WO | 2007118214 A2 | 10/2007 |
| WO | 2007126876 A2 | 11/2007 |
| WO | 2007141626 A1 | 12/2007 |
| WO | 2008005469 A2 | 1/2008 |
| WO | 2008079324 A1 | 7/2008 |
| WO | 2008079849 A2 | 7/2008 |
| WO | 2008098917 A2 | 8/2008 |
| WO | 2008108986 A2 | 9/2008 |
| WO | 2008115470 A2 | 9/2008 |
| WO | 2008116103 A2 | 9/2008 |
| WO | 2008144345 A2 | 11/2008 |
| WO | 2008144720 A2 | 11/2008 |
| WO | 2008152422 A2 | 12/2008 |
| WO | 2008155387 A2 | 12/2008 |
| WO | 2009005673 A1 | 1/2009 |
| WO | 2009006336 A1 | 1/2009 |
| WO | 2009016164 A1 | 2/2009 |
| WO | 2009017679 A2 | 2/2009 |
| WO | 2009019117 A1 | 2/2009 |
| WO | 2009021054 A2 | 2/2009 |
| WO | 2009032145 A1 | 3/2009 |
| WO | 2009032782 A2 | 3/2009 |
| WO | 2009039457 A1 | 3/2009 |
| WO | 2009045361 A2 | 4/2009 |
| WO | 2009045389 A2 | 4/2009 |
| WO | 2009079587 A2 | 6/2009 |
| WO | 2009120767 A1 | 10/2009 |
| WO | 2009126304 A1 | 10/2009 |
| WO | 2009137378 A2 | 11/2009 |
| WO | 2009137758 A2 | 11/2009 |
| WO | 2009149185 A2 | 12/2009 |
| WO | 2010034441 A1 | 4/2010 |
| WO | 2010036767 A1 | 4/2010 |
| WO | 2010045315 A1 | 4/2010 |
| WO | 2010048123 A2 | 4/2010 |
| WO | 2010052344 A1 | 5/2010 |
| WO | 2010062896 A1 | 6/2010 |
| WO | 2010066868 A2 | 6/2010 |
| WO | 2010069858 A1 | 6/2010 |
| WO | 2010075511 A1 | 7/2010 |

OTHER PUBLICATIONS

Casset, Roux, Mouchet, Bes, Chardes, Granier, Mani, Pugniere, Laune, Pau, Kaczorek, Lahana, and Rees. A peptide mimetic of an anti-CD4 monoclonal antibody by rational design. Biochemical and Biophysical Research Communications, 2003. vol. 307, pp. 198-205.*

Chen, Wiesmann, Fuh, Li, Christinger, Mc Kay, De Vos, and Lowman. Selection and analysis of an optimized anti-VEGF antibody: crystal structure of an affinity matured Fab in complex with antigen. Journal of Molecular Biology, 1999. vol. 293, pp. 865-881.*

Wu, Nie, Huse and Watkins. Humanization of a murine monoclonal antibody by simultaneous optimization of framework and CDR residues. Journal of Molecular Biology, 1999. vol. 294, pp. 151-162.*

Green. Antibody engineering via genetic engineering of the mouse: XenoMouse strains are a vehicle for the facile generation of therapeutic human monoclonal antibodies. Journal of Immunological Methods, 1999. vol. 231, pp. 11-23.*

Burtrum, Douglas, et al; A Fully Human Monoclonal Antibody to the Insulin-Like Growth Factor I Receptor Blocks Ligand-Dependent Signaling and Inhibits Human Tumor Growth in vivo; Cancer Research, American Association for Cancer Research (2003) vol. 63, No. 24 pp. 8912-8921.

Feng, Yang, et al; Novel Human Monoclonal Antibodies to Insulin-Like Growth Factor (IGF)-II that Potently Inhibit the IGF Receptor Type I Signal Transduction Function; Molecular Cancer Therapeutics, American Association of Cancer Research (2006) vol. 5, No. 1 pp. 114-120.

Mañes, Santos, et al; Functional Epitope Mapping of Insulin-Like Growth Factor I (IGF-I) by Anti-IGF-I Monoclonal Antibodies; Endocrinology (1997) vol. 138, No. 3 pp. 905-915.

Miyamoto, Shin'ichi, et al; Blockade of Paracrine Supply of Insulin-Like Growth Factors Using Neutralizing Antibodies Suppresses the Liver Metastasis of Human Colorectal Cancers; Clinical Cancer Research, The American Association for Cancer Research (2005) vol. 11, No. 9 pp. 3494-3502.

Zhao, Ronghua, et al; Positive Correlation of Insulin-Like Growth Factor-II with Proliferating Cell Index in Patients with Colorectal Neoplasia; Cancer Epidemiology Biomarkers & Prevention (2005) vol. 14, No. 7 pp. 1819-1822.

Rauchenberger, Robert, et al; Human Combinatorial Fab Library Yielding Specific and Functional Antibodies Against the Human Fibroblast Growth Factor Receptor 3-X; The Journal of Biological Chemistry (2003) vol. 278, No. 40 pp. 38194-38205.

Sell, Christian, et al; Effect of a Null Mutation of the Insulin-Like Growth Factor I Receptor Gene on Growth and Transformation of Mouse Embryo Fibroblasts; Molecular and Cellular Biology (1994) vol. 14, No. 6 pp. 3604-3612.

Shukla, Abhinav, A., et al; Downstream Processing of Monoclonal Antibodies—Application of Platform Approaches; Journal of Chromatography (2007) vol. 848 pp. 28-39.

Srinivasan, Mythily, et al; Immunomodulatory Peptides From IgSF Proteins: A Review; Current Protein and Peptide Science (2005) vol. 6, No. 2 pp. 185-196.

Strumberg, Dirk; Preclinical and Clinical Development of the Oral Multikinase Inhibitor Sorafenib in Cancer Treatment; Drugs of Today (2005) vol. 41, No. 12 pp. 773-784.

Takanami, Iwao, et al; Insulin-Like Growth Factor-II as a Prognostic Factor in Pulmonary Adenocarcinoma; Journal of Surgical Oncology (1996) vol. 61 pp. 205-208.

Tsai, J. F., et al; Serum Insulin-Like Growth Factor-II as a Serologic Marker of Small Hepatollular Carcinoma: Scandinavian Journal of Gastroenterology (2005) vol. 40 pp. 68-75.

Wang, Zheng, et al; Expression of IGF-II in Early Experimental Hepatocellular Carcinomas and its Significance in Early Diagnosis; World Journal of Gastroenterology (2003) vol. 9 pp. 267-270.

Woodson, Karen, et al; Loss of Insulin-Like Growth Factor-II Imprinting and the Presence of Screen-Detected Colorectal Adenomas in Women; Journal of the National Cancer Institute (2004) vol. 96, No. 5 pp. 407-410.

Yao, Xiaoming, et al; A Methylated Oligonucleotide Inhibits IGF2 Expression and Enhances Survival in a Model of Hepatocellular Carcinoma; The Journal of Clinical Investigation (2003) vol. 111, No. 2 pp. 265-273.

Yao, Xiaoming, et al; A Novel Orthotopic Tumor Model to Study Growth Factors and Oncogenes in Hepatocarcinogenesis; Clinical Cancer Research (2003) vol. 9 pp. 2719-2726.

Yelton, Dale, E. et al; Affinity Maturation of the BR96 Anti-Carcinoma Antibody by Codon-Based Mutagenesis; The American Association of Immunologists (1995) vol. 155 pp. 1994-2004.

Zapata, Gerardo, et al; Engineering Linear F(ab')2 Fragments for Efficient Production in *Escherichia coli* and Enhanced Antiproliferative Activity; Protein Engineering (1995) vol. 8, No. 10 pp. 1057-1062.

Barbas, Carlos F., et al; In Vitro evolution of a Neutralizing Human Antibody to Human Immunodeficiency Virus Type 1 to Enhance Affinity and Broaden Strain Cross-Reactivity; Proc. Natl. Acad. Sci. USA (1994) vol. 91 pp. 3809-1813.

Cascieri, Margaret, A., et al; Identification of the Insulin-Like Growth Factor I (IGF I) Epitopes Recognized by Monoclonal and Polyclonal Antibodies to IGF I; Endocrinology (1990) vol. 126, No. 6 pp. 2773-2777.

Chen, Jian-Wen, et al; Free Rather than Total Circulating Insulin-Like Growth Factor-I Determines the Feedback on Growth Hormone Release in Normal Subjects; The Journal of Clinical Endocrinology & Metabolism (2005) vol. 90, No. 1 pp. 366-371.

(56) References Cited

OTHER PUBLICATIONS

Chothia, Cyrus, et al; Canonical Structures for the Hypervariable Regions of Immunoglobulins; Journal Molecular Biology (1987) vol. 196 pp. 901-917.
Cui, Hengmi, et al; Loss of IGF2 Imprinting: A Potential Marker of Colorectal Cancer Risk; Science (2003) vol. 299 pp. 1753-1755.
Dufner, Almut, et al; Ribosomal S6 Kinase Signaling and the Control of Translation; Experimental Cell Research (1999) vol. 253 pp. 100-109.
EP Partial Search Report for EP08171554.2; Date: May 6, 2009, pp. 1-8.
European Search Report for EP 07110587.8. Date of completion: Mar. 18, 2008. pp. 1-9.
Frasca, F., et al; Insulin Receptor Isoform A, a Newly Recognized, High-Affinity Insulin-Like Growth Factor II Receptor in Fetal and Cancer Cells; Molecular and Cellular Biology (1999) vol. 19, No. 5 pp. 3278-3288.
Freier, S., et al; Expression of the Insulin-Like Growth Factors and their Receptors in Adenocarcinoma of the Colon; Gut (1999) vol. 44 pp. 704-708.
Fukuzawa, Ryuji, et al; High Frequency of Inactivation of the Imprinted H19 gene in "Sporadic" Hepatoblastoma; International Journal of Cancer (1999) vol. 82 pp. 490-497.
Goetsch, Liliane, et al; A Recombinant Humanized Anti-Insulin-Like Growth Factor Receptor Type I Antibody (h7C10) Enhances the Antitumor Activity of Vinorelbine and Anti-Epidermal Growth Factor Receptor Therapy Against Human Cancer Xenografts; International Journal of Cancer (2005) vol. 113 pp. 316-328.
Haenel, Cornelia et al; Characterization of High-Affinity Anitbodies by Electrochemiluminescense-Based Equilibrium Titration; (Analytical Biochemistry (2005) vol. 339 pp. 182-184.
Hassan, A. Bassim., et al; Insulin-Like Growth factor II Supply Modifies growth of Intestinal Adenoma in ApcMin/+ Mice1; Cancer Research (2000) vol. 60 pp. 1070-1076.
Hawkins, Robert E., et al; Selection of Phage Antibodies by Binding Affinity Mimicking Affinity Maturation; Journal Mol. Biol. (1992) vol. 226 pp. 889-896.
International Search Report for PCT/EP2008/057789 mailed Mar. 13, 2009.
International Search Report for PCT/EP2009/066894 mailed Jul. 15, 2010.
IPRP for PCT/EP2009/066894. Date of Issuance: Jun. 14, 2011; pp. 1-13.
Jackson, Jeffrey R., et al; In Vitro Antibody Maturation: Improvement of a High Affinity, Neutraizing Antibody Against IL-1b; Journal of Immunology (1995) vol. 154, No. 7 pp. 3310-3319.
Jerome L, et al; Deregulation of the IGF Axis in Cancer: Epidemiological Evidence and Potential Therapeutic Interventions; Endocrine-Related Cancer (2003) vol. 10 pp. 561-578.
Jirtle Randy L. "IGF2 Loss of Imprinting: A Potential Heritable Risk Factor for Colorectal Cancer"; Gastroenterology (2004) vol. 126 pp. 1190-1201.
Kipriyanov, Sergey M., et al; Generation and Production of Engineered Antibodies; Molecular Biotechnology (2004) vol. 26 pp. 39-60.
Knappik, Achim, et al; Fully Synthetic Human Combinatorial Antibody Libraries (HuCAL) Based on Modular Consensus Frameworks and CDRs Randomized with Trinucleotides; Journal Molecular Biology (2000) vol. 296 pp. 57-86.
Kolb, E. Anders, et al; Initial Testing (Stage 1) of a Monoclonal Antibody (SCH 717454) Against the IGF-1 Receptor by the Pediatric Preclinical Testing Program; Pediatr Blood Cancer (2008) vol. 50 pp. 1190-1197.
Krebs, Barbara, et al. "High-throughput generation and engineering of recombinant human antibodies" Journal of Immunological Methods 254 (2001) pp. 67-84.
Kulik, George et al; Antiapoptotic Signalling by the Insulin-Like Growth Factor I receptor, Phosphatidylinositol 3-Kinase, and AKt; Molecular and Cellular Biology (1997) vol. 17, No. 3 pp. 1595-1606.
Leroith, Derek; The Insulin-Like Growth Factor System; Experimental Diab. Res. (2003) vol. 4 pp. 205-212.
Li, Shu-Rui, et al; Differential Expression Patterns of the Insulin-Like Growth Factor 2 Gene in Human Colorectal Cancer; Tumor Biology (2004) vol. 25 pp. 62-68.
Lin, Yvonne, S., et al; Preclinical Pharmacokinetics, Interspecies scaling, and Tissue Distribution of a Humanized Monoclonal Antibody Against Vascular endothelial growth Factor; The Journal of Pharmacology and Experimental Thepapeutics (1999) vol. 288 pp. 371-378.
Lowman, Henry, B., et al; Selecting High-Affiniy Binding Proteins by Monovalent Phage Display; Biochemistry (1991) vol. 30, No. 45 pp. 10832-10837.
Lund, Per, et al; Autocrine Inhibition of Chemotherapy Response in Human Liver Tumor Cells by Insulin-Like Growth Factor-II; Cancer Letters (2004) vol. 206 pp. 85-96.
Manara, Maria C., et al; Preclinical in Vivo Study of New Insulin-Like Growth Factor-I Receptor-Specific Inhibitor in Ewing's Sarcoma; Clinical Cancer Research (2007) vol. 13, No. 4 pp. 1322-1330.
Manes, Santos, et al; Physical Mapping of Human Insulin-Like Growth Factor-I Using Specific Monoclonal Antibodies; Journal of endocrinology (1997) vol. 154 pp. 293-302.
Marks, James D., et al; By-Passing Immunization: Building High Affinity Human Antibodies by Chain Shuffling; Bio/Technology (1992) vol. 10 779-783.
Moorehead, Roger A., et al; Transgenic Overexpression of IGF-II Induces Spontaneous Lung Tumors: A Model for Human Lung Adenocarcinoma: Oncogene (2003) vol. 22 pp. 853-857.
Nagy, Zoltan A., et al; Fully Human, HLA -DR-Specific Monoclonal Anitbodies efficiently Induce Programmed Death of Malignant Lymphoid Cells; Nature Medicine (2002) vol. 8, Issue 8 pp. 801-807.
Ng, Irene OL, et al; "Hepatocellular Carcinoma Expression of Insulin-Like Growth Factor II mRNA in Hepatocellular Carcinoma" Journal of Gastroenterology and Hepatology (1998) vol. 13, p. 152-157.
Pandini, Giuseppe, et al.; "Insulin/Insulin-like Growth Factor I Hybrid Receptors Have Different Biological Characteristics Depending on the Insulin Receptor Isoform Involved"; The Journal of Biological Chemistry; (2002) V. 277, Issue: 42, pp. 39684-39695.
Pollak, Michael N. et al.; "Insulin-Like Growth Factors and Neoplasia" Nature Reviews Cancer, (2004) vol. 4, pp. 505-518.
Quinn, Kathryn A., et al; insulin-Like Growth Factor Expression in Human Cancer Cell Lines; The Journal of Biological Chemistry (1996) vol. 271, No. 19 pp. 11477-11483.
Reinberg, Steven "Rare Gene Mutation Plays Role in Longevity" Healthday News, published by US News & World Report, Mar. 4, 2008; pp. 1-3.
Renehan, Andrew, G., et al; Circulating Insulin-Like Growth Factor II and Colorectal Adenomas; The Journal of Clinical Endocrinology and Metabolism (2000) vol. 85, No. 9 pp. 3402-3408.
Renehan, Andrew, G., et al; Elevated Serum Insulin-Like Growth Factor (IGF)-II and IGF Binding Protein-2 in Patients with Colorectal Cancer; British Journal of Cancer (2000) vol. 83, No. 10 pp. 1344-1350.
Restriction Requirement mailed Feb. 22, 2012. U.S. Appl. No. 12/665,373, filed Mar. 31, 2010. Inventor: Paul Adam.
Revets, Hilde, et al; Nanobodies as Novel Agents for Cancer Therapy; Experts Opin. Biol. Ther. (2005) vol. 5, No. 1 pp. 111-124.
Rubin, Raphael, et al; Biology of Disease: Insulin-Like Growth Factor-I Receptor; Laboratory Investigation (1995) vol. 73, No. 3 pp. 311-331.
Rusell, William, E., et al; Inhibition of the Mitogenic Effects of Plasma by a Monoclonal Antibody to Somatomedin C; Proc. Natl. Acad. Sci. USA (1984) vol. 81 pp. 2389-2392.
Schier, Robert, et al; Identification of Functional and Structural Amino-Acid residues by Parsimonious Mutagenesis; Gene (1996) vol. 169 pp. 147-155.
Scotlandi, Katia, et al; Insulin-like Growth Factor I Receptor-Mediated Circuit in Ewing's Sarcoma/Peripheral Neuroectodermal Tumor: A Possible Therapeutic Target; Cancer Research (1996) vol. 56 pp. 4570-4574.

(56) References Cited

OTHER PUBLICATIONS

Goya, Masato, et al; Growth Inhibition of Human Prostate Cancer Cells in Human Adult Bone implanted into Nonobese Diabetic/Severe Combined Immunodeficient Mice by a Ligand-Specific Antibody to Human Insulin-Like Growth Factors; Cancer Research, American Association for Cancer Research (2004) vol. 64, No. 17 pp. 6252-6258.

Pollak, M.N., et al; Pharmacodynamic Properties of the Anti-IGF-IR Monoclonal Antibody CP-751,871 in Cancer Patients; American Society of Clinical Oncology (2007) vol. 25, No. 18S p. 3587.

Sell, Christian, et al; Simian Virus 40 Large Tumor Antigen is Unable to Transform Mouse Embryonic Fibroblasts lacking Type 1 Insulin-Like Growth Factor Receptor; Proc. Natl. Acad. Sci. USA (1993) vol. 90 pp. 11217-11221.

U.S. Appl. No. 13/653,843, filed Oct. 17, 2012, Inventor: Paul Adam.

* cited by examiner

VH3 Amino Acid Sequence:

QVELVESGGGLVQPGGSLRLSCAASGFTFSNXWMHWVRQAPGKGLEWVSGISGWSSWTYYADSVKGRFTISR
DNSKNTLYLQMNSLRAEDTAVYYCARFGIDAVTKVYFDYWGQGTLVTVSS

VH3 DNA Sequence:
CAGGTGGAATTGGTGGAAAGCGGCGGCGGCGGCCTGGTGCAACCGGGCGGCTCCCTGCGTCTGAGCTGCGCGGCCTCCGGATTTACCTT
TTCTAATTATTGGATGCATTGGGTGCGCCAAGCCCCTGGGAAGGTCTCGAGTGGGTGAGCGGTATCTCTGGTTGGTCTA
GCTGGACCTATTATGCGGATAGCGTGAAAGGCCGTTTTACCATTCACGTGATAATTCGAAAAACACCCTGTATCTGCAA
ATGAACAGCCTGCGTGCGGAAGATACGGCCGTGTATTATTGCGCGCGCGTTTTGGTATTGATGCTTATACTAAGGTTTATTT
TGATTATTGGGGCCAAGGCACCCTGGTGACGGTTAGCTCA

40186

Vλ3 Amino Acid Sequence:

DIELTQPPSVSVAPGQTARISCSGDNIELKKYVSWYQQKPGQAPVLVIHDDNKRPSGIPERFSGSNSGNTA
TLTISGTQAEDEADYYCQSWASTGVVFGGGTKLTVLG (Q)

Vλ3 DNA Sequence:
GATATCGAACTGACCCAGCCGCCTTCAGTGAGCGTTGCACCAGGTCAGACCGCGCGTATCTCGTGTAGCGGCGATAATAT
TCCTCTTAAGTATGTTCTTGGTACCAGCAGCAGAAACCCGGGCCAGGCGCCAGTTCTTGTGATTCATGATGATAAGCGTC
CCTCAGGCATCCCGGAACGCTTTAGCGGCATCCAACAGCGGCACTAGGCCACTCAGGCGAA
GACGAAGCGGATTATTATTGCCAGTCTTGGGCTTCTACTGGTGTTGTTTTCTACTGGTGTTGTTGGCGGCACGAAGTTAACCGTCCTAGGT

VH3 Amino Acid Sequence:
QVELVESGGGLVQPGGSLRLSCAASGFTWSSFAMSWVRQAPGKGLEWVSYISTLGSYTGYADSVKGRFTISR
DNSKNTLYLQMNSLRAEDTAVYYCARGTKFDYWGQGTLVTVSS VH3 DNA Sequence:
CAGGTGGAATTGGTGGAAAGCGGCGGCGGCCTGGTGCAACCGGGCGGCCTGAGCTGCGCCGCCTCCGGATTTACCTG
GTCTTCTTTTGCTATGTCTTGGGTGCGCCAAGCCCCCGGAAAGGGTCTCGAGTGGTGAGCTATATCTCTTATCTTGGTA
GCTATACCGGTTATGCGGATAGCGTGAAAGGCCGTTTTACCATTTCACGTGATAATTCGAAAAAACACCCTGTATCTGCAA
ATGAACAGCCTGCGCGCGGAAGATACGGCCGTGTATTATTGCGCGCGCGTGGTACTAAGTTTGATTATTGGGGCCAAGGCAC
CCTGGTGACGGTTAGCTCA

40183

Vλ1 Amino Acid Sequence:
DIVLTQPPSVSGAPGQRVTISCTGSSSNIGTYYDVHWYQQLPGTAPKLLIYSNSKRPSGVPDRFSGSKSGTS
ASLAITGLQSEDEADYYCSITRVFGGGTKLTVLG (Q)

Vλ1 DNA Sequence:
GATATCGTGCTGACCCAGCCGCCTTCAGTGAGTGGCGCACCAGGTCAGCGTGTGACCATCTCGTGTACGGGCAGCAGCAG
CAACATTGGTACTTATGATGTGCATTGGTACCAGCAGTTGCCCGGAACGGCCCCGAAACTTCTGATTTATTCTAATTCTA
AGCGTCCCTCAGGCGTGCCGGATCGTTTAGCGGATCCAAAAGCGGCACCAGCGCCTTGCGAGCCTTGCGATTACGGCCTGCAA
AGCGAAGACGAAGCGGATTACTATTGCTCTCTATTACTCGTGTGTTTGGCGGCGGCACGAAGTTAACCGTCCTAGGT

ANTI-IGF ANTIBODIES

This application is a national phase entry under 35 U.S.C. 371 of international application PCT/EP2008/057789, filed Jun. 19, 2008, which claims priority to European Application No. EP 07110587.8, filed Jun. 19, 2007, each of which is hereby incorporated by reference in its entirety.

The present invention relates to the therapy of hyperproliferative diseases, in particular to the therapy of cancers.

BACKGROUND OF THE INVENTION

Insulin-like growth factor-1 (IGF-1; a 70 amino-acid polypeptide) and insulin-like growth factor-2 (IGF-2; a 67 amino-acid polypeptide) are 7.5-kD soluble factors present in serum that can potently stimulate the growth of many mammalian cells (reviewed by Pollack et al., 2004). Although IGFs can be detectable in a number of tissues the main source of circulating IGFs is the liver which secretes the IGFs and IGF binding proteins (IGFBPs) in response to a complex signaling pathway that is initiated in the pituitary gland and transduced via growth hormone. On secretion into the bloodstream the IGFs form complexes with the IGFBPs which not only protects them from proteolytic degradation in the serum en route to their target tissues but also prevents their association with the IGF receptors. In addition to this endocrine source of IGFs they are also known to be secreted in an autocrine or paracrine manner in target tissues themselves. This is known to occur during normal fetal development where the IGFs play a key role in the growth of tissues, bone and organs. It is also seen in many cancer tissues where there is thought to be paracrine signaling between tumour cells and stromal cells or autocrine IGF production by the tumour cells themselves (reviewed by LeRoith D, 2003).

The activity of the IGFs is thought to be regulated by a complex and relatively poorly understood interaction involving seven different IGFBPs and other serum proteins. Activation of the IGFs involves their release from this ternary complex after proteolytic release of the serum binding protein and IGFBPs, this is thought to occur in close proximity to cell surfaces where the IGFs are then free to bind to their receptors and transduce intracellular signals that ultimately leads to cellular proliferation and the inhibition of apoptosis. IGF-1 and IGF-2 are able to bind to the IGF-1 receptor (IGF-1R) expressed on many normal tissues, which functionally is a 460 kD heterotetramer consisting of a dimerised alpha- and beta-subunit, with similar affinities (Rubin et al., 1995). IGF-2 can also bind to the IGF-2 receptor (also know as the mannose-6-phosphate receptor) which does not have any known signaling function, rather it is thought to act as a sink for IGF-2 and prevent it from binding and signaling through the IGF-1R. In this respect the IGF-2R has been demonstrated to be a tumour suppressor protein. The IGF-1R is structurally similar to the insulin receptor which exists in two forms, IR-A and IR-B, which differ by an alternatively spliced 12 amino acid exon deletion in the extracellular domain of IR-A. IR-B is the predominant IR isoform expressed in most normal adult tissues where it acts to mediate the effects of insulin on metabolism. IR-A on the other hand is known to be highly expressed in developing fetal tissues but not in adult normal tissues. Recent studies have also shown that IR-A, but not IR-B, is highly expressed in some cancers. The exon deletion in IR-A has no impact on insulin binding but does cause a small conformational change that allows IGF-2 to bind with much higher affinity than for IR-B (Frasca et al., 1999; Pandini et al., 2002). Thus, because of it's expression in cancer tissues and increase propensity for IGF-2 binding, IR-A may be as important as IGF1-R in mediating the mitogenic effects of IGF-2 in cancer.

Binding of the IGFs to IGF-1R triggers a complex intracellular signaling cascade which results in activation of proteins that stimulate growth and inhibit apoptosis (reviewed by Pollack et al., 2004). In terms of growth, upregulated translation is induced by the activation of p70 S6 kinase, which in turn phosphorylates the S6 ribosomal protein (Dufner and Thomas, 1999). Thus, IGF-stimulated cell growth can be measured by the rapid increase in phosphorylated S6 ribosomal protein.

Unlike the EGFR and Her2neu receptors there is no known amplification of the IGF1-R or IR-A receptors in cancers indicating that receptor activation is controlled by the presence of active ligand. There is a very large body of scientific, epidemiological and clinical literature implicating a role for the IGFs in the development, progression and metastasis of many different cancer types (reviewed by Jerome et al., 2003; and Pollack et al., 2004).

For example, in colorectal cancer the expression of IGF-2 mRNA and protein is elevated in clinical colorectal tumour specimens compared with adjacent normal tissue (Freier et al., 1999; Li et al., 2004). There is also a positive correlation of elevated IGF serum levels with proliferating cell index in patients with colorectal neoplasia (Zhao et al., 2005). In addition, elevated circulating levels of IGF-2 correlate with an increased risk of developing colorectal cancers and adenomas (Renehan et al., 2000a) and b); Hassan et al., 2000). Loss of parental imprinting (LOI) of the IGF-2 gene, an epigenetic alteration that results in elevated IGF-2 expression, is a heritable molecular trait that has recently been identified in patients with colorectal and other tumour types. Loss of IGF-2 imprinting has been shown to be associated with a five-fold risk of colorectal neoplasia (Cui et al., 2003; Cruz-Correa et al., 2004) and adenomas (Woodson et al., 2004). Antibodies targeting the alpha-subunit of the IGF-1R which block IGF binding and internalize the receptor have been shown to delay the growth of the xenografted colon cancer-derived cell lines such as COLO 205 (Burtrum et al., 2003).

Elevated levels of IGFs are associated with a poor prognosis in human pulmonary adenocarcinomas (Takanami et al., 1996) and IGFs are expressed and secreted by many SCLC— and NSCLC-derived cell lines (Quinn et al., 1996). Transgenic over-expression of IGF-2 induces spontaneous lung tumours in a murine model (Moorhead et al., 2003). In terms of hepatocellular carcinoma (HCC), human clinical specimens and animal models of HCC express higher levels of IGF mRNA and protein than corresponding normal tissues and this has been correlated with increased tumour growth (Wang et al., 2003; Ng et al., 1998). IGF-2 has also been shown to be a serological marker of HCC with elevated levels in the serum of HCC patients compared with controls (Tsai et al., 2005). An orthotopic xenograft tumour model of HCC was established using Hep 3B cells, and used to demonstrate that inhibition of IGF-2 expression using a methylated oligonucleotide enhances survival (Yao et al., 2003a) and b).

Many childhood solid tumours such as Ewing sarcoma and rhabdomyosarcoma appear to be particularly dependent on the IGF signaling pathway for their growth (Scotlandi et al., 1996). LOI of the IGF-2 gene has been implicated as a primary genetic event in the development for embryonal rhabdomyosarcoma (Fukuzawa et al., 1999). Autocrine IGF signaling is also thought to strongly influence the growth of Ewing sarcoma in cases where the type-1 EWS-FLI1 chimeric transcription factor is expressed through a chromosomal translocation resulting in elevated expression of target genes including the IGF ligands and IGF-1R, and reduced expression of IGFBP-3. Antibodies and small molecule compounds targeting the IGF-1R have been shown to reduce the growth of xenografted pediatric solid tumour derived cell lines (Kolb et al., 2008; Manara et al., 2007).

Using IGF ligand-specific antibodies it has been demonstrated that the growth of human prostate cancer cells in adult human bone implanted into SCID mice can be inhibited (Goya et al., 2004). In addition, it was demonstrated that the same IGF ligand antibodies could block the paracrine supply of IGF and suppress the liver metastasis of human colorectal cancer cells in a murine xenograft system (Miyamoto et al., 2005).

There is also considerable evidence suggesting that the IGF signaling system reduces the sensitivity of cancers to chemotherapeutic agents and radiation. One of the earliest findings in this respect was the demonstration that IGF-1R knock-out mouse embryos are refractory to transformation by viruses, oncogenes and over-expressed growth factor receptors (Sell et al., 1993; Sell et al., 1994) and that over-expression of IGF-1R protects cells from UV irradiation and gamma radiation-induced apoptosis (Kulik et al., 1997). Furthermore, using liver tumour cell lines that secrete large amounts of IGF-2, it was found that neutralization of IGF-2 significantly increased response to chemotherapeutic agents such as cisplatin and etoposide in vitro, especially at lower, cytostatic doses, suggesting that IGF-2 can reduce the susceptibility to chemotherapeutic agents (Lund et al., 2004). Consistent with these findings it has been demonstrated that antibodies targeting the IGF-1R increase the susceptibility of tumour xenografts to growth inhibition by chemotherapeutic drugs and radiation (Goetsch et al., 2005).

A number of antibodies that show cross-reactive binding to human IGF-1 and human IGF-2 have been reported. Antibody sm1. was raised against human IGF-1 and shows 40% cross-reactivity to human IGF-2 and was shown to inhibit the proliferation of a mouse fibroblast cell line BALB/c3T3 which was stimulated with 20 ng/ml human IGF-1 (Russell et al., 1984). In a study designed to functionally epitope map IGF-1 by raising monoclonal antibodies to whole IGF-1 protein and portions of the protein a number of antibodies where identified that cross reacted with IGF-2 (Manes et al., 1997). The percent cross-reactivity with IGF-2 ranged from 0 to 800% and several antibodies were identified which were equally IGF-1 and IGF-2 reactive. KM1486 is a rat monoclonal antibody that cross-reacts with human IGF-1 and IGF-2 and it was demonstrated that KM1486 can inhibit growth of human prostate cancer cells in human adult bone implanted into nonobese diabetic/severe combined immunodeficient mice (Goya et al., 2004). In addition, it was demonstrated that KM1486 suppresses the liver metastasis of human colorectal cancers (Miyamoto et al., 2005). KM1486 has also been described in WO 03/093317, JP 2003-310275, WO 2005/018671, WO 2005/028515, and WO 2005/027970.

For the treatment of human disease an antibody with a fully human sequence is highly desirable in order to minimize the risk of generating a human anti-antibody reaction and neutralizing antibodies that will rapidly eliminate the administered antibody from the body and thereby reduce the therapeutic effect. As such, and given the roles of IGF-1 and IGF-2 dependent signaling in the development and progression of cancers it would be desirable to obtain high affinity fully human antibodies that co-neutralise the mitogenic effects of both ligands.

In addition, to maximize the therapeutic potential of such an antibody, it is important to have a suitably long terminal half life ($T_{1/2}$). Prior to terminal half life determination in human subjects, the most accurate estimation of an antibody's human terminal half life can be obtained from administration to non-human primates such as cynomolgus monkeys. For example, bevacizumab, a registered humanized monoclonal antibody against vascular endothelial growth factor (VEGF) used for the treatment of several human cancers, has a terminal half-life in cynomolgus monkeys of 8.57±0.38 days (Lin et al., 1999), which translates to a terminal half life in humans of approximately 20 days allowing for a single administration once every two weeks (Lu et al., 2008).

It was a further object of the invention to obtain an antibody that does not affect binding of insulin to its receptor.

The clinical development of therapeutic agents is supported by pharmacodynamic biomarkers of drug activity. Clinical studies with antibodies targeting the IGF-1R have demonstrated that an increase in total serum IGF-1 levels may be a useful pharmacodynamic marker for these agents (Pollack et al., 2007). The reason for the increase in total serum IGF-1 levels is likely due to a feedback mechanism involving pituitary growth hormone (GH) secretion which releases both IGF-1 and IGFBPs from the liver. Indeed, in humans it has been demonstrated that free or bioactive IGF-1, which represents only around 1% of total IGF-1 levels, determines the feedback response (Chen et al., 2005). The inventors thus sought to confirm whether total serum IGF-1 levels are also a useful pharmacodynamic marker for the activity of a therapeutic anti-IGF antibody. In this case it would be desirable for such antibody to be cross-reactive with IGFs from a suitable animal species, e.g. mouse or rat, such that a pharmacodynamic effect can already be tested pre-clinically.

BRIEF DESCRIPTION OF THE FIGURES

FIG. 9 shows the amino acid and DNA sequences of the variable chains of antibodies 40186(A) and 40183(B); CDRs are highlighted.

BRIEF DESCRIPTION OF INVENTION

Figure 1A:
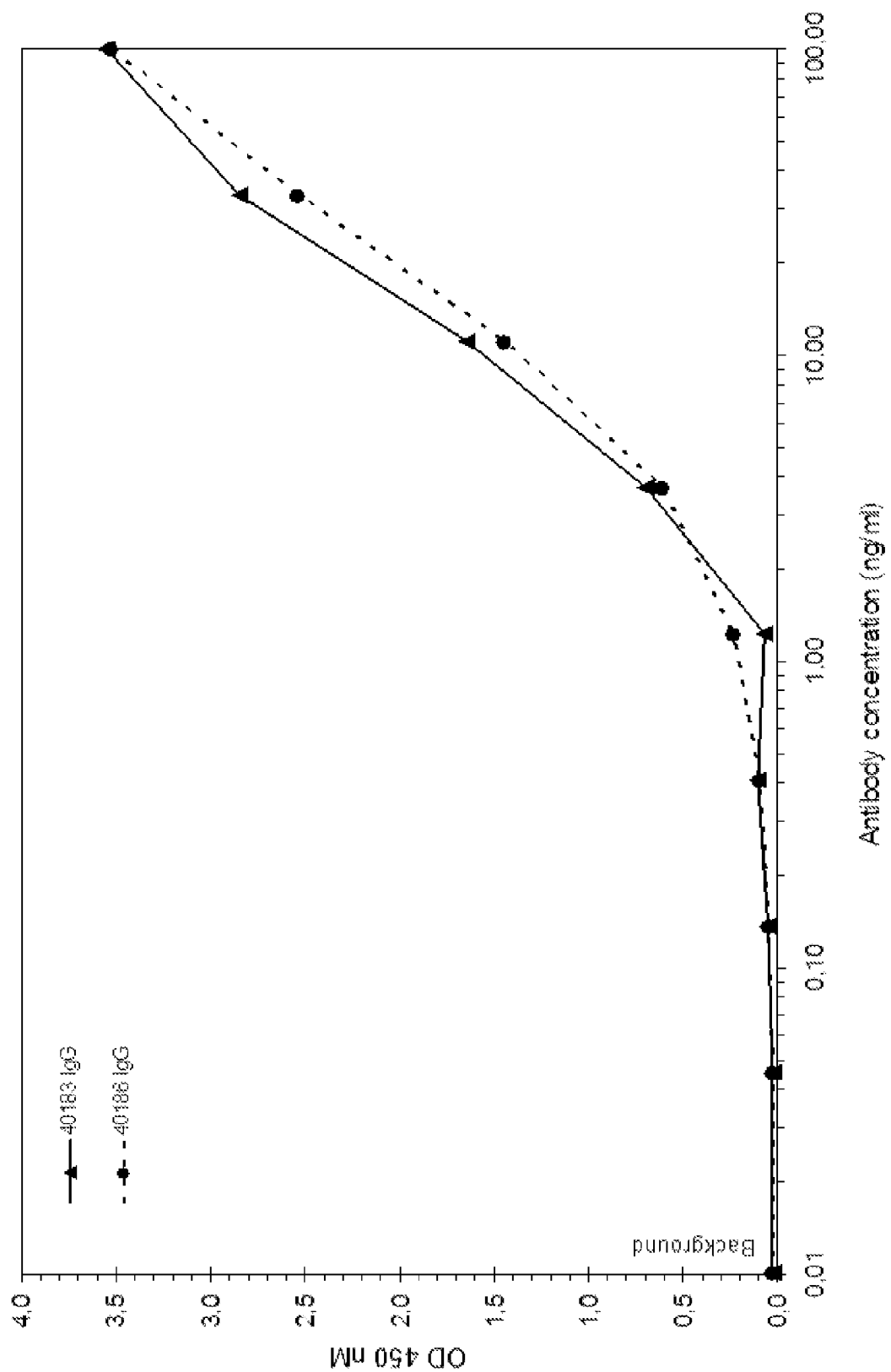
FIGS. 1A-1H show an ELISA binding titration of IgG1 antibodies 40183 and 40186 to human IGF-1 (FIG. 1A), human IGF-2 (FIG. 1B), murine IGF-1 (FIG. 1C), murine IGF-2 (FIG. 1D), rat IGF-1 (FIG. 1E), rat IGF-2 (FIG. 1F), human insulin (FIG. 1G) and coating plastic control (FIG. 1H).
Figure 1B:
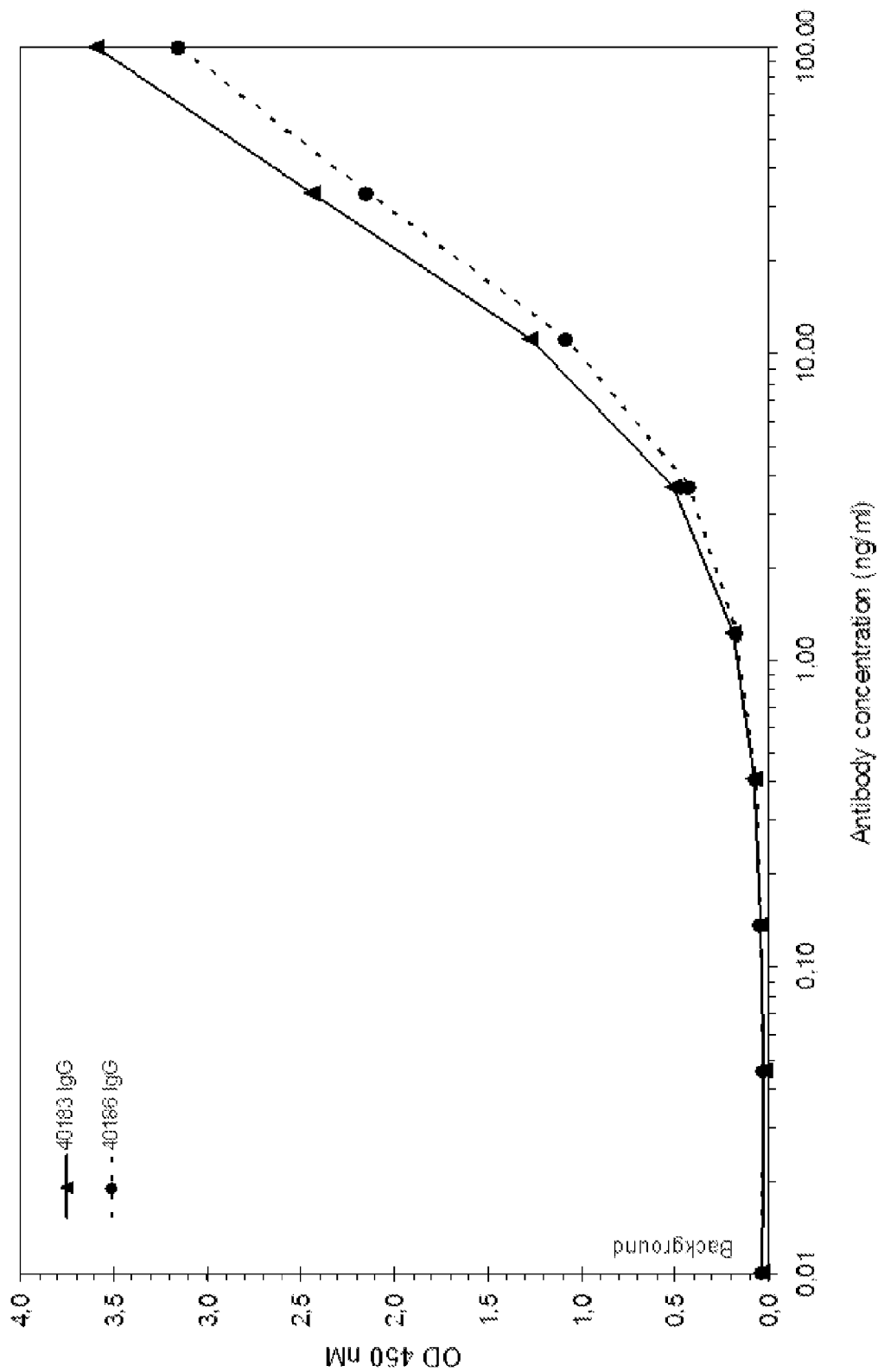
Figure 1C:
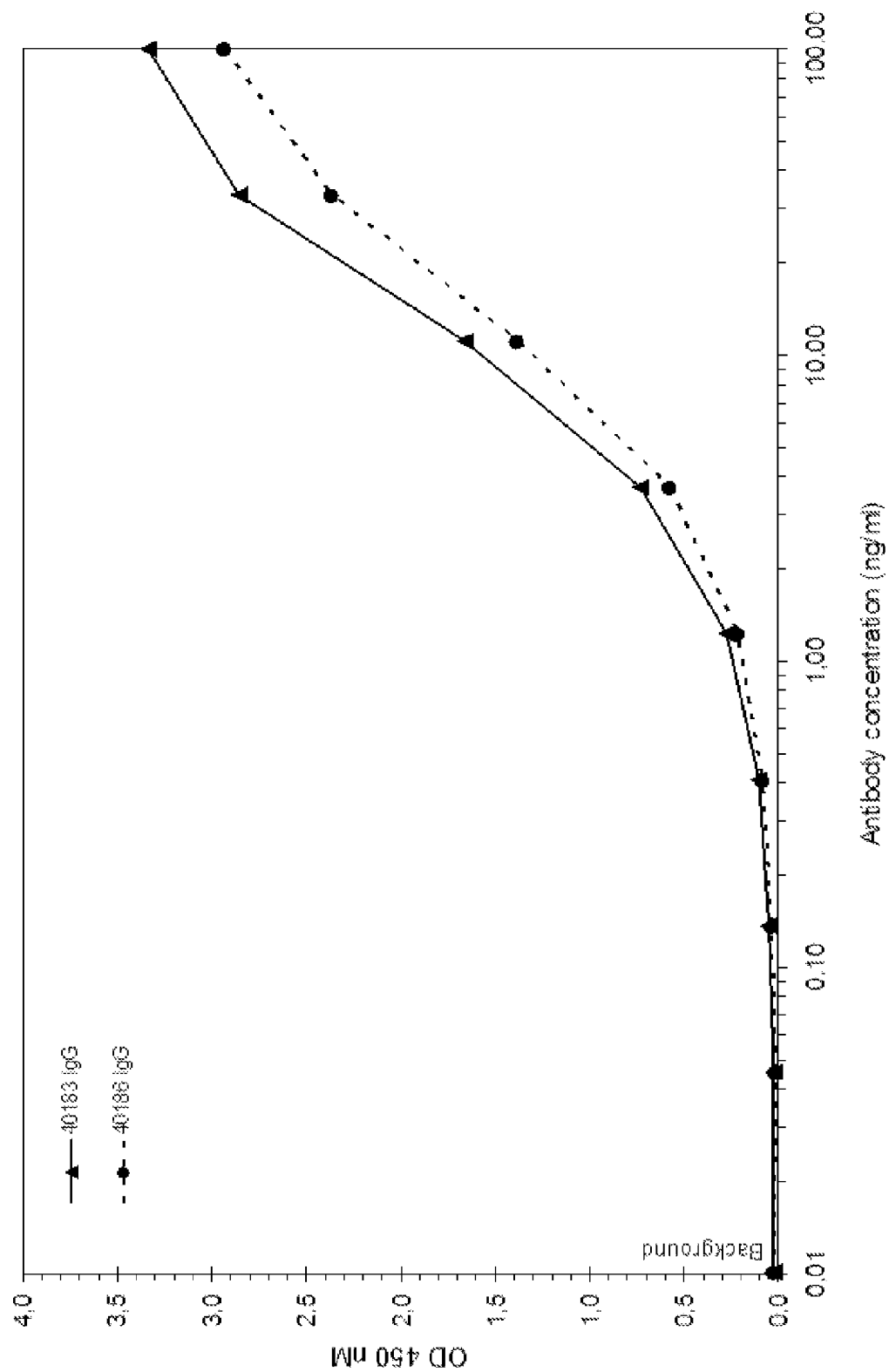
Figure 1D:
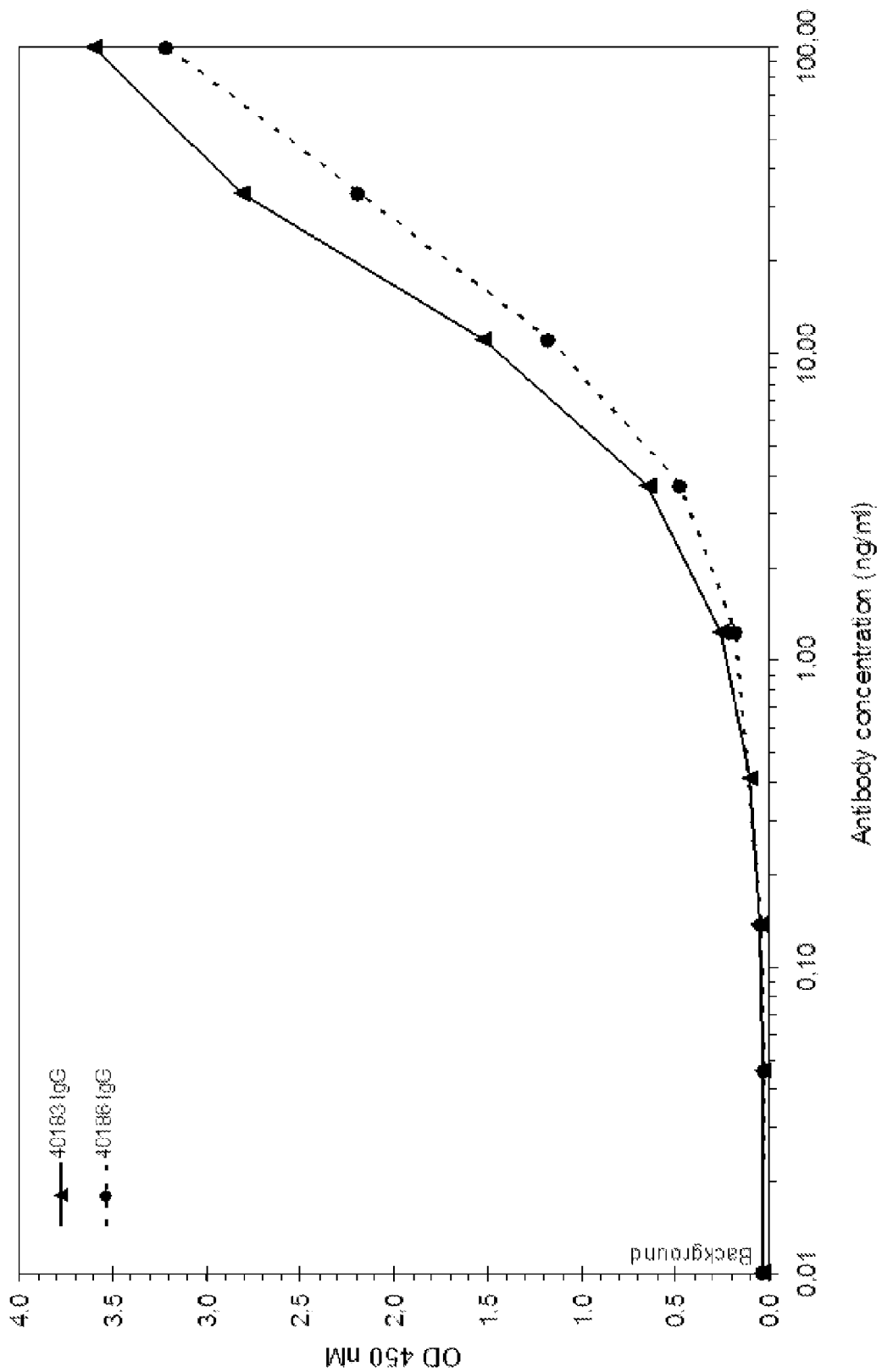
Figure 1E:
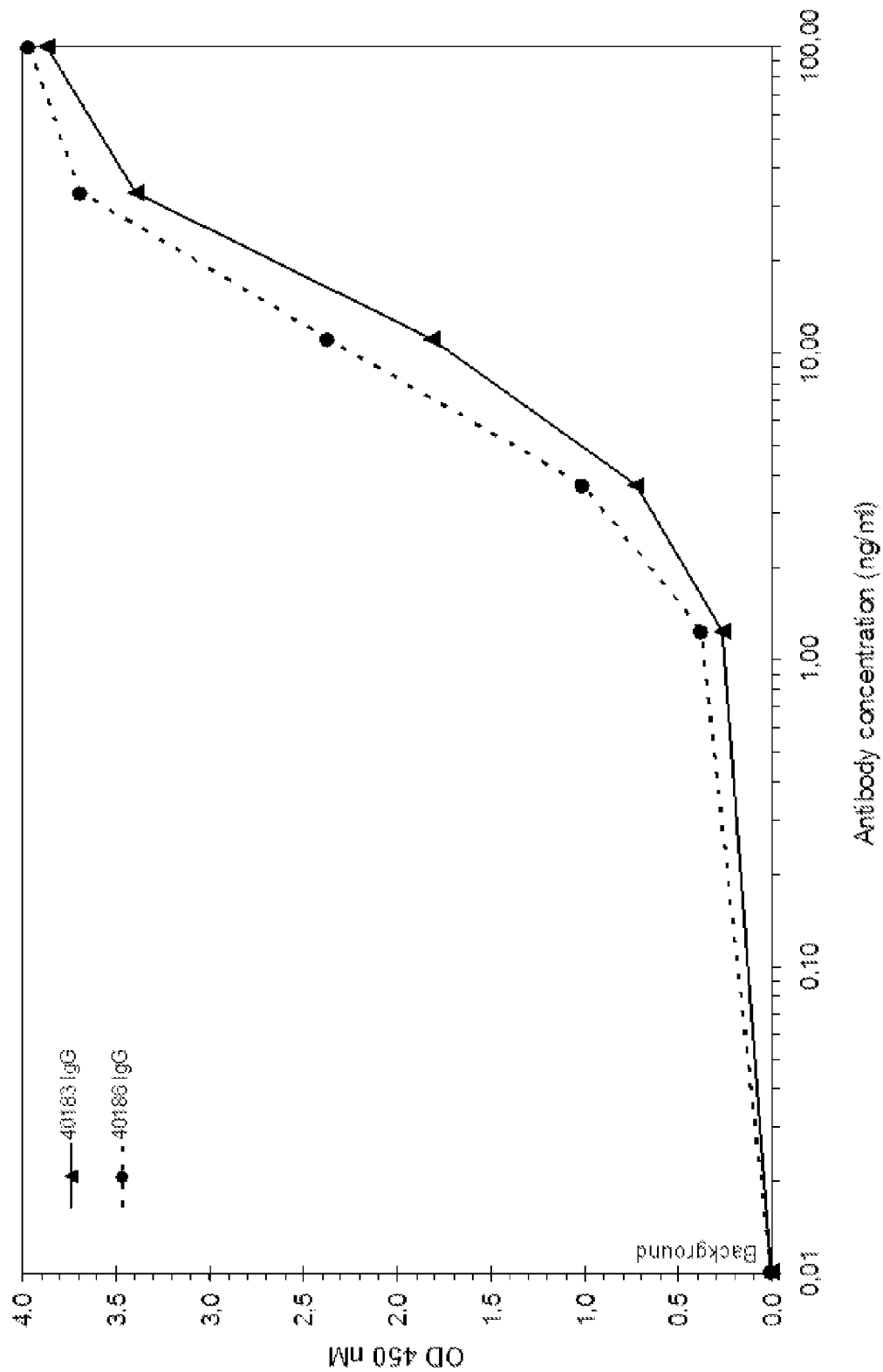
Figure 1F:
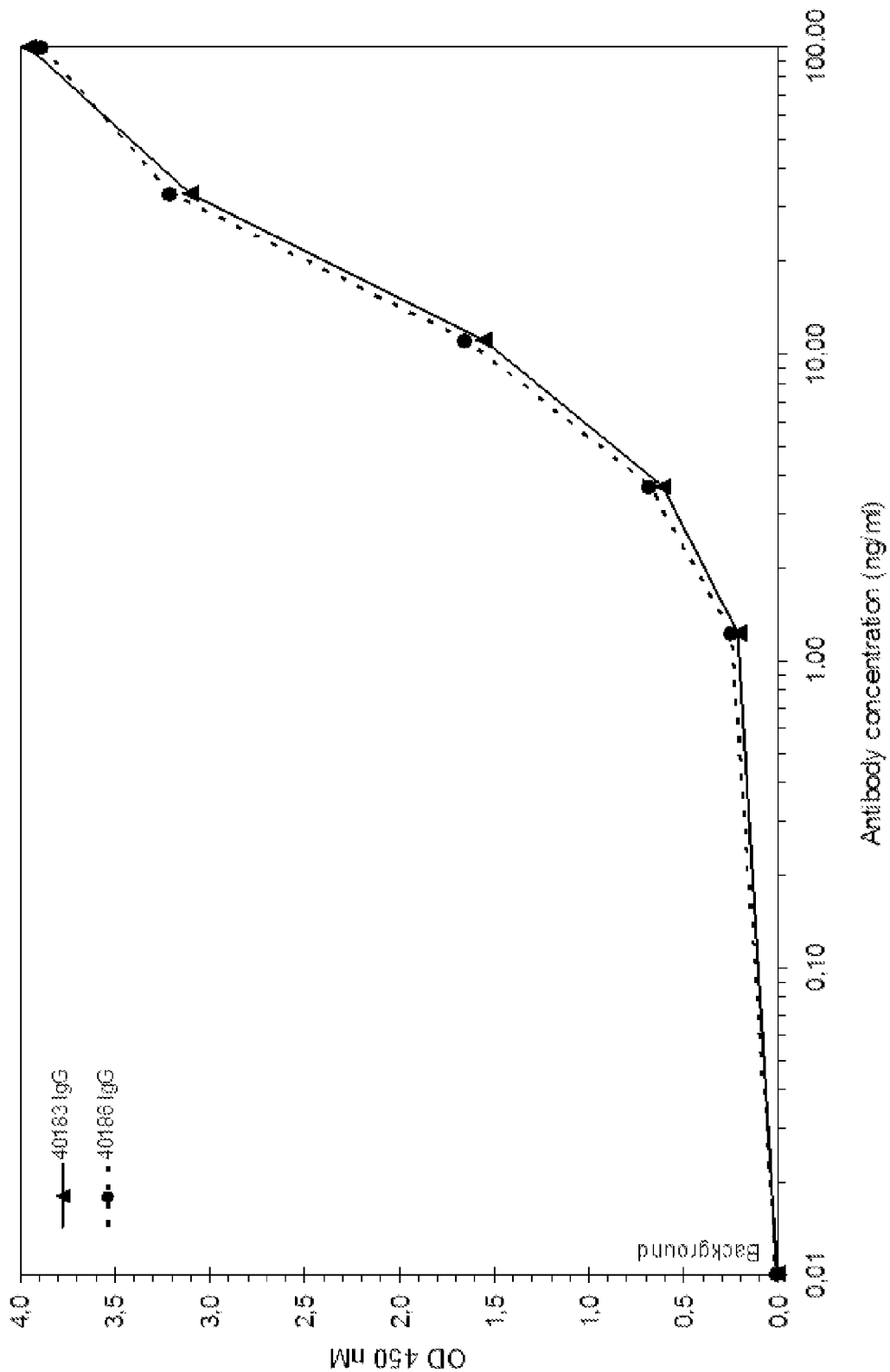
Figure 1G:
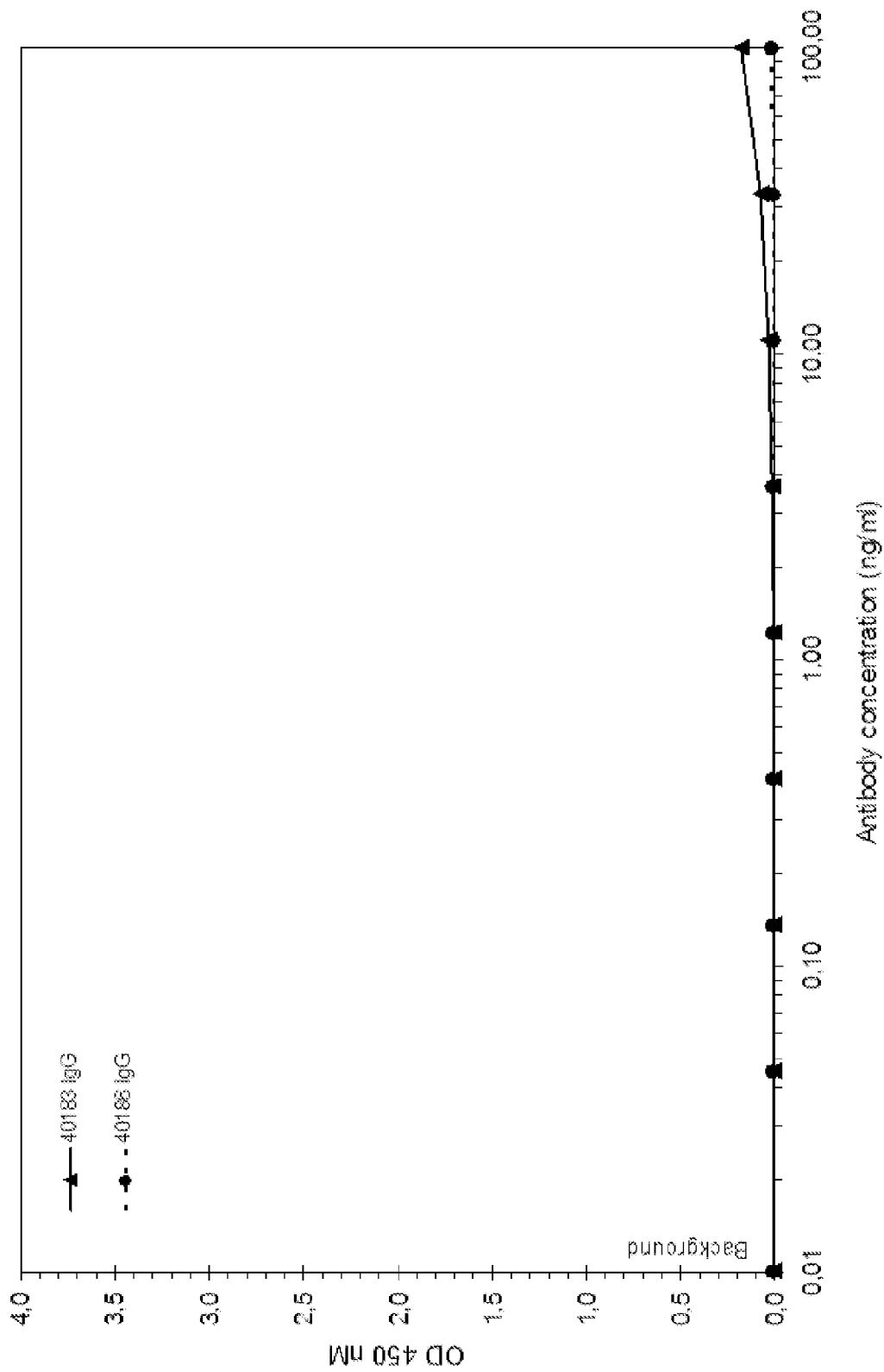
Figure 1H:
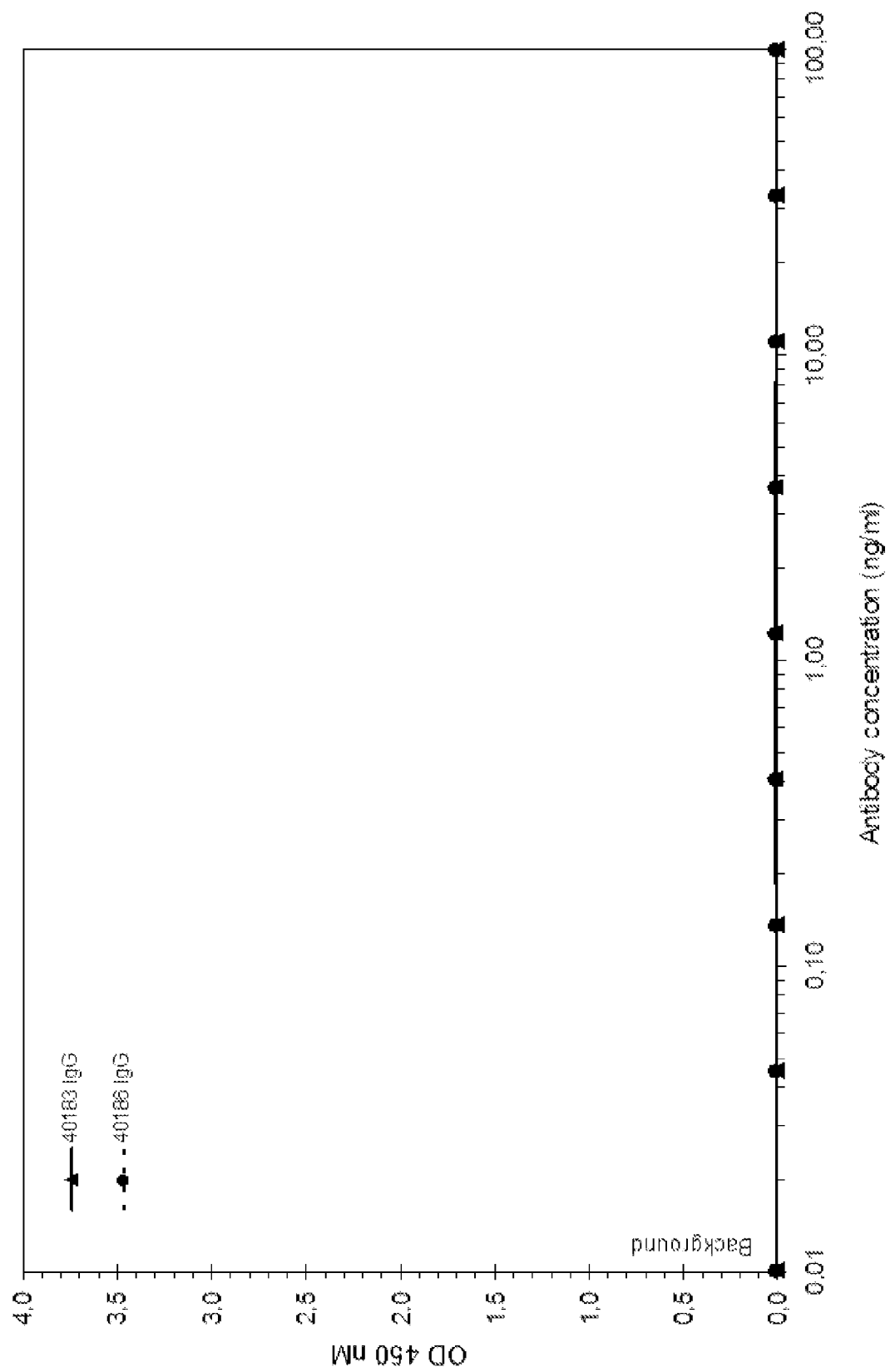

The present invention relates to an isolated human antibody molecule, which
a) binds to human IGF-1 and IGF-2 such that
   i) binding of IGF-1 and IGF-2 to the IGF-1 receptor is prevented and
   ii) IGF-1 receptor-mediated signaling is inhibited,
b) binds to murine and rat IGF-1 and IGF-2,
c) does not bind to human insulin,
d) does not affect the mitogenic properties of human insulin that are mediated by its binding to the insulin receptors.

Binding of the antibody is defined as the interaction that occurs via the non-covalent bonds that hold the antigen (or a protein or a fragment thereof that is structurally similar) to the antibody combining site, i.e. the region of the immunoglobulin that combines with the determinant of an appropriate antigen (or a structurally similar protein).

Affinity (i.e. the interaction between a single antigen-binding site on an antibody and a single epitope) is expressed by the association constant $K_A = k_{ass}/k_{diss}$ or the dissociation constant $K_D = k_{diss}/k_{ass}$.

According to a), the antibody binds to each IGF protein with an affinity, as determined by surface plasmon resonance analysis, with a $K_D$ value ranging from ca. 1 nM to ca. 7 nM, in particular, with an affinity of ca. 4 nM.

According to a), the antibody binds to each IGF protein with an affinity, as determined by surface plasmon resonance analysis, with a $K_D$ value ranging from ca. 1 nM to ca. 7 nM, in particular, with an affinity of ca. 4 nM. Based on this property, neutralization of IGF functional signaling is achieved.

According to c), the antibody does not bind to human insulin at concentrations that are at least 100-fold higher than the minimum concentration required for binding to human IGF-1 or IGF-2.

In general, a mitogenic property is defined as the ability of a compound to encourage a cell to commence cell division, triggering mitosis, e.g. in the case of insulin, its ability to promote cell growth.

The property of the anti-IGF antibody molecule defined in d) is characterized by the fact that the affinity of the anti-IGF antibody molecule to IGF-1 and IGF-2, respectively, is at least 100-fold, and even more than 1000-fold, as compared to its affinity to insulin. Even though at very high doses, e.g. more than 100 mg/kg, weak binding may not be completely excluded, the anti-IGF antibody molecule does not bind to insulin at therapeutic doses.

In addition to its ability to inhibit IGF-1 receptor-mediated signaling, an antibody of the invention preferably also has the ability to inhibit IGF-2 induced signaling through the insulin receptor IR-A.

DETAILED DESCRIPTION OF THE INVENTION

In the following, an antibody molecule of the invention, which binds to human IGF-1 and IGF-2, is termed "anti-IGF antibody molecule".

The term "anti-IGF antibody molecule" encompasses human anti-IGF antibodies, anti-IGF antibody fragments, anti-IGF antibody-like molecules and conjugates with any of the above mentioned antibody molecules. Antibodies include, in the meaning of the present invention, but are not limited to, monoclonal, chimerized monoclonal, and bi- or multispecific antibodies. The term "antibody" shall encompass complete immunoglobulins as they are produced by lymphocytes and for example present in blood sera, monoclonal antibodies secreted by hybridoma cell lines, polypeptides produced by recombinant expression in host cells, which have the binding specificity of immunoglobulins or monoclonal antibodies, and molecules which have been derived from such immunoglobulins, monoclonal antibodies, or polypeptides by further processing while retaining their binding specificity.

In particular, the term "antibody molecule" includes complete immunoglobulins comprising two heavy chains and two light chains, preferably, fully human antibodies.

In a further aspect, the antibody molecule is an anti-IGF antibody-fragment that has an antigen binding region. To obtain antibody fragments, e.g. Fab fragments, digestion can be accomplished by means of routine techniques, e.g. using papain or pepsin. Examples of papain digestion are described in WO 94/29348 and U.S. Pat. No. 4,342,566. Papain digestion of antibodies typically produces two identical antigen binding fragments, so-called Fab fragments, each with a single antigen binding site, and a residual Fc fragment. Pepsin treatment yields an F(ab')$_2$ fragment that has two antigen combining sites and is still capable of cross-linking the antigen. Antibody fragments can also be generated by molecular biology methods producing the respective coding DNA fragments.

Fab fragments also contain the constant domains of the light chain and the first constant domain (CH$_1$) of the heavy chain. Fab' fragments differ from Fab fragments in that they contain additional residues at the carboxy terminus of the heavy chain CH$_1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them.

Antigen-binding antibody fragments or antibody-like molecules, including single-chain antibodies and linear antibodies as described in Zapata et al., 1995, may comprise, on a single polypeptide, the variable region(s) alone or in combination with the entirety or a portion of the following: constant domain of the light chain, CH1, hinge region, CH2, and CH3 domains, e.g. a so-called "SMIP" ("Small Modular Immunopharmaceutical"), which is an anti-body like molecule employing a single polypeptide chain as its binding domain Fv, which is linked to single-chain hinge and effector domains devoid of the constant domain CH1 (WO 02/056910). SMIPs can be prepared as monomers or dimers, but they do not assume the dimer-of-dimers structure of traditional antibodies. Also included in the invention are antigen-binding fragments comprising any combination of variable region(s) with a constant domain region of a light chain, VH1, CH1, hinge region, CH2, and CH3 domains.

The antibody fragments or antibody-like molecules may contain all or only a portion of the constant region as long as they exhibit specific binding to the relevant portion of the IGF-1/IGF-2 antigen. The choice of the type and length of the constant region depends, if no effector functions like complement fixation or antibody dependent cellular toxicity are desired, mainly on the desired pharmacological properties of the antibody protein. The antibody molecule will typically be a tetramer consisting of two light chain/heavy chain pairs, but may also be dimeric, i.e. consisting of a light chain/heavy chain pair, e.g. a Fab or Fv fragment, or it may be a monomeric single chain antibody (scFv).

The anti-IGF antibody-like molecules may also be single domain antibodies (e.g. the so-called "nanobodies"), which harbour an antigen-binding site in a single Ig-like domain (described e.g. in WO 03/050531, and by Revets et al., 2005).

Other examples for antibody-like molecules are immunoglobulin super family antibodies (IgSF; Srinivasan and Roeske, 2005), or CDR-containing or CDR-grafted molecules or "Domain Antibodies" (dAbs). dABs are functional binding units of antibodies, corresponding to the variable regions of either the heavy (VH) or light (VL) chains of human antibodies. Domain Antibodies have a molecular weight of approximately 13 kDa, or less than one-tenth the size of a full antibody. A series of large and highly functional libraries of fully human VH and VL dAbs has been developed. dABs are also available for "dual targeting", i.e. dAbs that bind, in addition to IGF-1/IGF-2, to a further target in one molecule. dAb libraries, selection and screening methods, dAb formats for dual targeting and for conferring extended serum half life are described in e.g. U.S. Pat. No. 6,696,245, WO 04/058821, WO 04/003019, and WO 03/002609.

In general, antibody fragments and antibody-like molecules are well expressed in bacterial, yeast, and mammalian cell systems.

In a preferred embodiment, the anti-IGF antibody of the invention is a fully human, recombinant complete antibody comprising two heavy chains and two light chains.

In a preferred embodiment, the anti-IGF antibody molecule has a heavy chain CDR3 comprising the amino acid sequence of SEQ ID NO:3. Preferably, the antibody has a light chain CDR3 comprising the amino acid sequence of SEQ ID NO:6. Preferably, the antibody further has a heavy chain CDR1 comprising the amino acid sequence of SEQ ID NO:1 and a heavy chain CDR2 comprising the amino acid sequence of SEQ ID NO:2. Preferably, the antibody further has a light chain CDR1 comprising the amino acid sequence of SEQ ID NO:4 and a light chain CDR2 comprising the amino acid sequence of SEQ ID NO:5.

In a preferred embodiment, the antibody has the variable regions of the antibody designated 40186, with a variable heavy chain comprising the amino acid sequence of SEQ ID NO:14 and a variable light chain comprising the amino acid sequence of SEQ ID NO:16 (this sequence may contain, at its C-terminus, an additional Gln. This amino acid position may either be considered the C-terminal end of the variable region, according to the Kabat numbering, or alternatively, and in line with the sequences in the sequence listing, it may represent the first amino acid of the constant light chain, see SEQ ID NO:24).

Preferably, an antibody with the variable heavy chain comprising the amino acid sequence of SEQ ID NO:14 and a variable light chain comprising the amino acid sequence of SEQ ID NO:16 has an IgG1 constant heavy chain region. Preferably, such antibody has an Igλ constant light chain region.

Preferably, the antibody is the antibody designated 40186, which has a heavy chain constant region which comprises the amino acid sequence of SEQ ID NO:22 and a light chain constant region which comprises the amino acid sequence of SEQ ID NO:24.

The complete amino acid sequences of the antibody designated 40186 are depicted in SEQ ID NO:25 (heavy chain) and SEQ ID NO:26 (light chain).

In a further preferred embodiment, the anti-IGF antibody molecule has a heavy chain CDR3 comprising the amino acid sequence of SEQ ID NO:9.

Preferably, the antibody has a light chain CDR3 comprising the amino acid sequence of SEQ ID NO:12. Preferably, the antibody further has a heavy chain CDR1 comprising the amino acid sequence of SEQ ID NO:7 and a heavy chain CDR2 comprising the amino acid sequence of SEQ ID NO:8. Preferably, the antibody further has a light chain CDR1 comprising the amino acid sequence of SEQ ID NO:10 and a light chain CDR2 comprising the amino acid sequence of SEQ ID NO:11.

In a preferred embodiment, the antibody has the variable regions of the antibody 40183 that has a variable heavy chain comprising the amino acid sequence of SEQ ID NO:18 and a variable light chain comprising the amino acid sequence of SEQ ID NO:20 (this sequence may contain, at its C-terminus, an additional Gln; see above).

In a preferred embodiment, the antibody is the antibody designated 40183 that has the identical constant chain regions as antibody 40186, i.e. a heavy chain constant region which comprises the amino acid sequence of SEQ ID NO:22 and a light chain constant region which comprises the amino acid sequence of SEQ ID NO:24.

CDRs ("Complementarity Determining Regions") of a monoclonal antibody are understood to be those amino acid sequences involved in specific antigen binding according to Kabat et al., 1991, in connection with Chothia and Lesk, 1987.

It could be demonstrated in xenograft models of cancer that the antibodies of the invention are useful to treat human diseases.

The cross-reactivity of the antibodies of the invention with murine and rat IGF-1 allows to examine their endocrine effects, e.g. the effect on the growth hormone pathway, in these species. The observed pharmacodynamic effect of the antibodies on total IGF-1 levels, likely due to removal of the free IGF-1, which results in feedback regulation through the growth hormone pathway resulting in increased secretion of IGF-1 and IGFBP3 by the liver, is a useful pharmacodynamic marker. The availability of such marker in animal species, which allows determination of a dose/effect relationship early in drug development, facilitates the preparation of Phase I clinical studies where, in addition to PK analysis, the pharmacodynamic response on total IGF-1 and IGFBP3 levels in patients are monitored.

Another advantage of the antibodies of the invention is their superior half-life; it has been shown that antibody 40186 has a half-life in cynomolgus in the range from $10.7 \pm 1.6$ days (1 mg/kg) to $12 \pm 1.4$ (10 mg/kg).

The anti-IGF antibody molecule of the invention may also be a variant of an antibody as defined by the amino acid sequences shown in the sequence listing. Thus, the invention also embodies antibodies that are variants of these polypeptides, which have the features a) to d) defined above. Using routinely available technologies, the person skilled in the art will be able to prepare, test and utilize functional variants of the antibodies 40183 and 40186. Examples are variant antibodies with at least one position in a CDR and/or framework altered, variant antibodies with single amino acid substitutions in the framework region where there is a deviation from the germline sequence, antibodies with conservative amino substitutions, antibodies that are encoded by DNA molecules that hybridize, under stringent conditions, with the DNA molecules presented in the sequence listing encoding antibody variable chains of 40183 or 40186, functionally equivalent codon-optimised variants of 40183 and 40186.

A variant may also be obtained by using an antibody of the invention as starting point for optimization and diversifying one or more amino acid residues, preferably amino acid residues in one or more CDRs, and by screening the resulting collection of antibody variants for variants with improved properties. Particularly preferred is diversification of one or more amino acid residues in CDR3 of the variable light chain, CDR3 of the variable heavy chain, CDR1 of the variable light and/or CDR2 of the variable heavy chain. Diversification can be done by methods known in the art, e.g. the so-called TRIM technology referred to in WO 2007/042309.

Given the properties of individual amino acids, rational substitutions can be performed to obtain antibody variants that conserve the overall molecular structure of antibody 40183 or 40186. Amino acid substitutions, i.e., "conservative substitutions", may be made, for instance, on the basis of similarity in polarity, charge, solubility, hydrophobicity, hydrophilicity, and/or the amphipathic nature of the respective amino acid. The skilled person is familiar with commonly practiced amino acid substitutions, as described e.g. in WO 2007/042309, and methods for obtaining thus modified antibodies. Given the genetic code and recombinant and synthetic DNA techniques, DNA molecules encoding variant antibodies with one or more conservative amino acid exchanges can be routinely designed and the respective antibodies readily obtained. In one particular example, amino acid position 3 in the variable heavy chains SEQ ID NOS: 14 and 18 has been changed from a Q (which is the naturally occurring amino acid at this position) to an E; in a variant antibody within the scope of the present invention, E may be changed back to Q.

In comparison with antibodies 40183 or 40186 of the present invention, preferred antibody variants have a sequence identity in the CDR regions of at least 60%, more preferably, at least 70% or 80%, still more preferably at least 90% and most preferably at least 95%. Preferred antibodies also have a sequence similarity in the CDR regions of at least 80%, more preferably 90% and most preferably 95%. Preferred antibody variants have a sequence identity in the variable regions of at least 60%, more preferably, at least 70% or 80%, still more preferably at least 90% and most preferably at least 95%. Preferred antibodies also have a sequence similarity in the variable regions of at least 80%, more preferably 90% and most preferably 95%.

("Sequence identity" between two polypeptide sequences indicates the percentage of amino acids that are identical between the sequences. "Sequence similarity" indicates the percentage of amino acids that either are identical or that represent conservative amino acid substitutions.)

In a further embodiment, the anti-IGF antibody molecule of the invention is an "affinity matured" antibody.

An "affinity matured" anti-IGF antibody is an anti-IGF antibody derived from a parent anti-IGF antibody, e.g. 40186, or 40183, that has one or more alterations in one or more CDRs which result in an improvement in the affinity for the antigens, compared to the respective parent antibody. One of the procedures for generating such antibody mutants involves phage display (Hawkins et al., 1992; and Lowman et al., 1991). Briefly, several hypervariable region sites (e.g. 6-7 sites) are mutated to generate all possible amino substitutions at each site. The antibody mutants thus generated are displayed in a monovalent fashion from filamentous phage particles as fusions to the gene III product of M13 packaged within each particle. The phage-displayed mutants are then screened for their biological activity (e.g. binding affinity) as herein disclosed.

Affinity matured antibodies may also be produced by methods as described, for example, by Marks et al., 1992, (affinity maturation by variable heavy chain (VH) and variable light chain (VL) domain shuffling), or Barbas et al., 1994; Shier et al., 1995; Yelton et al., 1995; Jackson et al., 1995; and Hawkins et al., 1992, (random mutagenesis of CDR and/or framework residues). Preferred affinity matured antibodies will have nanomolar or even picomolar affinities for the target antigen.

Affinity matured anti-IGF antibodies may also be obtained by the RapMAT™ technology, recently introduced by Morp hoSys. RapMAT™ represents an in-built affinity maturation process for the rapid selection of high affinity antibodies. Basis for this technology is the modular concept of MorphoSys's HuCAL technology (Knappik et al., 2000). In the HuCAL libraries complementarity-determining regions (CDRs), which define the binding site of the antibody and thus its capabilities to bind a specific target molecule, can easily be exchanged in a simple cloning step. Using RapMAT™, the uncharacterized polyclonal output after two rounds of standard selection is used and diversity is increased by insertion of a pre-built CDR cassette library. This is in contrast to HuCAL's standard maturation process, where individual antibody candidates are selected and matured by subsequent CDR exchange. Subsequently two further selection rounds are applied under high stringency conditions to select for high affinity. This ultimately leads to the direct selection of antibodies with an up to 40-fold increased affinity for their target molecule.

The present invention also relates to DNA molecules that encode an anti-IGF antibody molecule of the invention. These sequences include, but are not limited to, those DNA molecules encoding antibodies 40183 and 40186 as shown in the sequence listing: SEQ ID NO:13 and SEQ ID NO:15, respectively, encoding the variable heavy and light chain, respectively, of antibody 40186; SEQ ID NO:17 and SEQ ID NO:19, encoding the variable heavy and light chain, respectively, of antibody 40183; SEQ ID NO:15 and SEQ ID NO:19, encoding the variable light chains, may, at their 3' end, contain an additional codon for Gln.

Accordingly, the present invention also relates to nucleic acid molecules that hybridize to the DNA molecules set forth in the sequence listing under high stringency binding and washing conditions, as defined in WO 2007/042309, where such nucleic molecules encode an antibody or functional fragment thereof that has properties equivalent or superior to antibody 40183 or 40186. Preferred molecules (from an mRNA perspective) are those that have at least 75% or 80% (preferably at least 85%, more preferably at least 90% and most preferably at least 95%) homology or sequence identity with one of the DNA molecules described herein.

Yet another class of DNA variants that are within the scope of the invention may be defined with reference to the polypeptide they encode. These DNA molecules deviate with respect to their sequence from those depicted in the sequence listing (SEQ ID NOs: 13, 15, 19 and 20), but encode, due to the degeneracy of the genetic code, antibodies with the identical amino acid sequences of antibody 40183 or 40186, respectively. By way of example, in view of expressing antibodies 40183 or 40186 in eukaryotic cells, the last nine nucleotides of SEQ ID NO:19 and 17, respectively, that encode the last three amino acids of the variable light chains, have been designed to match codon usage in eukaryotic cells. If it is desired to express the antibodies in E. coli, these sequences can be changed to match E. coli codon usage (e.g. GTT CTT GGC instead of GTC CTA GGT as shown in SEQ ID NO:19 and 15).

Variants of DNA molecules of the invention can be constructed in several different ways, as described in WO 2007/042309.

For producing the recombinant anti-IGF antibody molecules of the invention, the DNA molecules (cDNA and/or genomic DNA) encoding full-length light chain (in the case of antibody 40186, a sequence comprising SEQ ID NO:15 and SEQ ID NO:23) and heavy chain (in the case of antibody 40186, the sequence comprising SEQ ID NO:13 and SEQ ID NO:21) or fragments thereof are inserted into expression vectors such that the sequences are operatively linked to transcriptional and translational control sequences.

For manufacturing the antibodies of the invention, the skilled artisan may choose from a great variety of expression systems well known in the art, e.g. those reviewed by Kipriyanow and L Gall, 2004.

Expression vectors include plasmids, retroviruses, cosmids, EBV derived episomes, and the like. The expression vector and expression control sequences are selected to be compatible with the host cell. The antibody light chain gene and the antibody heavy chain gene can be inserted into separate vectors. In certain embodiments, both DNA sequences are inserted into the same expression vector. Convenient vectors are those that encode a functionally complete human CH (constant heavy) or CL (constant light) immunoglobulin sequence, with appropriate restriction sites engineered so that any VH (variable heavy) or VL (variable light) sequence can be easily inserted and expressed, as described above. In the case of the antibodies with the variable regions of 40183 and 40186, the constant chain is usually kappa or lambda for the antibody light chain, for the antibody heavy chain, it can be, without limitation, any IgG isotype (IgG1, IgG2, IgG3, IgG4) or other immunoglobulins, including allelic variants.

The recombinant expression vector may also encode a signal peptide that facilitates secretion of the antibody chain from a host cell. The DNA encoding the antibody chain may be cloned into the vector such that the signal peptide is linked in-frame to the amino terminus of the mature antibody chain DNA. The signal peptide may be an immunoglobulin signal peptide or a heterologous peptide from a non-immunoglobulin protein. Alternatively, the DNA sequence encoding the antibody chain may already contain a signal peptide sequence.

In addition to the antibody chain DNA sequences, the recombinant expression vectors carry regulatory sequences including promoters, enhancers, termination and polyadenylation signals and other expression control elements that control the expression of the antibody chains in a host cell. Examples for promoter sequences (exemplified for expression in mammalian cells) are promoters and/or enhancers derived from CMV (such as the CMV Simian Virus 40 (SV40) promoter/enhancer), adenovirus, (e.g., the adenovirus major late promoter (AdMLP)), polyoma and strong mammalian promoters such as native immunoglobulin and actin promoters. Examples for polyadenylation signals are BGH polyA, SV40 late or early polyA; alternatively, 3'UTRs of immunoglobulin genes etc. can be used.

The recombinant expression vectors may also carry sequences that regulate replication of the vector in host cells (e.g. origins of replication) and selectable marker genes. Nucleic acid molecules encoding the heavy chain or an antigen-binding portion thereof and/or the light chain or an antigen-binding portion thereof of an anti-IGF antibody, and vectors comprising these DNA molecules can be introduced into host cells, e.g. bacterial cells or higher eukaryotic cells, e.g. mammalian cells, according to transfection methods well known in the art, including liposome-mediated transfection, polycation-mediated transfection, protoplast fusion, microinjections, calcium phosphate precipitation, electroporation or transfer by viral vectors.

Preferably, the DNA molecules encoding the heavy chain and the light chain are present on two vectors which are co-transfected into the host cell, preferably a mammalian cell.

Mammalian cell lines available as hosts for expression are well known in the art and include, inter alia, Chinese hamster ovary (CHO) cells, NSO, SP2/0 cells, HeLa cells, baby hamster kidney (BHK) cells, monkey kidney cells (COS), human carcinoma cells (e.g., Hep G2), A549 cells, 3T3 cells or the derivatives/progenies of any such cell line. Other mammalian cells, including but not limited to human, mice, rat, monkey and rodent cells lines, or other eukaryotic cells, including but not limited to yeast, insect and plant cells, or prokaryotic cells such as bacteria may be used. The anti-IGF antibody molecules of the invention are produced by culturing the host cells for a period of time sufficient to allow for expression of the antibody molecule in the host cells.

Antibody molecules are preferably recovered from the culture medium as a secreted polypeptide or it can be recovered from host cell lysates if for example expressed without a secretory signal. It is necessary to purify the antibody molecules using standard protein purification methods used for recombinant proteins and host cell proteins in a way that substantially homogenous preparations of the antibody are obtained. By way of example, state-of-the art purification methods useful for obtaining the anti-IGF antibody molecule of the invention include, as a first step, removal of cells and/or particulate cell debris from the culture medium or lysate. The antibody is then purified from contaminant soluble proteins, polypeptides and nucleic acids, for example, by fractionation on immunoaffinity or ion-exchange columns, ethanol precipitation, reverse phase HPLC, Sephadex chromatography, chromatography on silica or on a cation exchange resin. As a final step in the process for obtaining an anti-IGF antibody molecule preparation, the purified antibody molecule may be dried, e.g. lyophilized, as described below for therapeutic applications.

In a further aspect, the present invention relates to a pharmaceutical composition containing, as the active ingredient, an anti-IGF antibody molecule, preferably a full antibody, of the invention.

To be used in therapy, the anti-IGF antibody molecule is included into pharmaceutical compositions appropriate to facilitate administration to animals or humans. Typical formulations of the anti-IGF antibody molecule can be prepared by mixing the anti-IGF antibody molecule with physiologically acceptable carriers, excipients or stabilizers, in the form of lyophilized or otherwise dried formulations or aqueous solutions or aqueous or non-aqueous suspensions. Carriers, excipients, modifiers or stabilizers are nontoxic at the dosages and concentrations employed. They include buffer systems such as phosphate, citrate, acetate and other anorganic or organic acids and their salts; antioxidants including ascorbic acid and methionine; preservatives such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); proteins, such as serum albumin, gelatin, or immunoglobulins; hydrophilic polymers such as polyvinylpyrrolidone or polyethylene glycol (PEG); amino acids such as glycine, glutamine, asparagine, histidine, arginine, or lysine; monosaccharides, disaccharides, oligosaccharides or polysaccharides and other carbohydrates including glucose, mannose, sucrose, trehalose, dextrins or dextrans; chelating agents such as EDTA; sugar alcohols such as, mannitol or sorbitol; salt-forming counter-ions such as sodium; metal complexes (e.g., Zn-protein complexes); and/or ionic or non-ionic surfactants such as TWEEN™ (polysorbates), PLURONICS™ or fatty acid esters, fatty acid ethers or sugar esters. Also organic solvents can be contained in the antibody formulation such as ethanol or isopropanol. The excipients may also have a release-modifying or absorption-modifying function.

The anti-IGF antibody molecules may also be dried (freeze-dried, spray-dried, spray-freeze dried, dried by near or supercritical gases, vacuum dried, air-dried), precipitated or crystallized or entrapped in microcapsules that are prepared, for example, by coacervation techniques or by interfacial polymerization using, for example, hydroxymethylcellulose or gelatin and poly-(methylmethacylate), respectively, in colloidal drug delivery systems (for example, liposomes, albumin microspheres, microemulsions, nano-particles and nanocapsules), in macroemulsions or precipitated or immobilized onto carriers or surfaces, for example by pcmc technology (protein coated microcrystals). Such techniques are disclosed in Remington, 2005.

Naturally, the formulations to be used for in vivo administration must be sterile; sterilization may be accomplished be conventional techniques, e.g. by filtration through sterile filtration membranes.

It may be useful to increase the concentration of the anti-IGF antibody to come to a so-called high concentration liquid formulation (HCLF); various ways to generate such HCLFs have been described.

The anti-IGF antibody molecule may also be contained in a sustained-release preparation. Such preparations include solid, semi-solid or liquid matrices of hydrophobic or hydrophilic polymers, and may be in the form of shaped articles, e.g., films, sticks or microcapsules and may be applied via an application device. Examples of sustained-release matrices include polyesters, hydrogels (for example, poly(2-hydroxy-ethyl-methacrylate or sucrose acetate butyrate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilization (e.g. as described in WO 89/011297) from acidic solutions, controlling moisture content, using appropriate additives, and developing specific polymer matrix compositions.

Formulations that may also be used for the anti-IGF antibody molecule of the invention are described in U.S. Pat. No. 7,060,268 and U.S. Pat. No. 6,991,790.

The IGF antibody molecule can be incorporated also in other application forms, such as dispersions, suspensions or liposomes, tablets, capsules, powders, sprays, transdermal or intradermal patches or creams with or without permeation enhancing devices, wafers, nasal, buccal or pulmonary formulations, or may be produced by implanted cells or—after gene therapy—by the individual's own cells.

An anti-IGF antibody molecule may also be derivatized with a chemical group such as polyethylene glycol (PEG), a methyl or ethyl group, or a carbohydrate group. These groups may be useful to improve the biological characteristics of the antibody, e.g., to increase serum half-life or to increase tissue binding.

The preferred mode of application is parenteral, by infusion or injection (intravenous, intramuscular, subcutaneous, intraperitoneal, intradermal), but other modes of application such as by inhalation, transdermal, intranasal, buccal, oral, may also be applicable.

In a preferred embodiment, the pharmaceutical composition of the invention contains the anti-IGF-antibody, e.g. antibody 40186, in a concentration of 10 mg/ml and further comprises 25 mM Na citrate pH 6, 115 mM NaCl, 0.02% Tween (polysorbate 20).

For the prevention or treatment of disease, the appropriate dosage of antibody will depend on the type of disease to be treated, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

Depending on the type and severity of the disease, about 1 μg/kg to 20 mg/kg (e.g. 0.1-15 mg/kg) of antibody is an initial candidate dosage for administration to the patient, whether, for example, by one or more separate administrations, or by continuous infusion. A typical treatment schedule usually involves administration of the antibody once every week to once every three weeks with doses ranging from about 0.1 μg/kg to ca. 20 mg/kg or more, depending on the factors mentioned above. progress of this therapy is easily monitored by conventional techniques and assays.

The "therapeutically effective amount" of the antibody to be administered is the minimum amount necessary to prevent, ameliorate, or treat a disease or disorder.

The anti-IGF antibody molecule of the invention and pharmaceutical compositions containing it are useful for the treatment of hyperproliferative disorders.

In certain embodiments, the hyperproliferative disorder is cancer.

Cancers are classified in two ways: by the type of tissue in which the cancer originates (histological type) and by primary site, or the location in the body, where the cancer first developed. The most common sites in which cancer develops include the skin, lung, breast, prostate, colon and rectum, cervix and uterus.

The anti-IGF antibody molecules of the invention are useful in the treatment of a variety of cancers, including but not limited to the following:

AIDS-related cancer such as Kaposi's sarcoma;

bone related cancer such as Ewing's family of tumours and osteosarcoma;

brain related cancer such as adult brain tumour, childhood brain stem glioma, childhood cerebellar astrocytoma, childhood cerebral astrocytoma/malignant glioma, childhood ependymoma, childhood medulloblastoma, childhood supratentorial primitive neuroectodermal tumours, childhood visual pathway and hypothalamic glioma and other childhood brain tumours;

breast cancer;

digestive/gastrointestinal related cancer such as anal cancer, extrahepatic bile duct cancer, gastrointestinal carcinoid tumour, cholangiocarcinoma, colon cancer, esophageal cancer, gallbladder cancer, adult primary liver cancer (hepatocellular carcinoma, hepatoblastoma) childhood liver cancer, pancreatic cancer, rectal cancer, small intestine cancer and stomach (gastric) cancer;

endocrine related cancer such as adrenocortical carcinoma, gastrointestinal carcinoid tumour, islet cell carcinoma (endocrine pancreas), parathyroid cancer, pheochromocytoma, pituitary tumour and thyroid cancer;

eye related cancer such as intraocular melanoma, and retinoblastoma;

genitourinary related cancer such as bladder cancer, kidney (renal cell) cancer, penile cancer, prostate cancer, transitional cell renal pelvis and ureter cancer, testicular cancer, urethral cancer, Wilms' tumour and other childhood kidney tumours;

germ cell related cancer such as childhood extracranial germ cell tumour, extragonadal germ cell tumour, ovarian germ cell tumour and testicular cancer;

gynecologic cancer such as cervical cancer, endometrial cancer, gestational trophoblastic tumour, ovarian epithelial cancer, ovarian germ cell tumour, ovarian low malignant potential tumour, uterine sarcoma, vaginal cancer and vulvar cancer;

head and neck related cancer such as hypopharyngeal cancer, laryngeal cancer, lip and oral cavity cancer, metastatic squamous neck cancer with occult primary, nasopharyngeal cancer, oropharyngeal cancer, paranasal sinus and nasal cavity cancer, parathyroid cancer and salivary gland cancer;

hematologic/blood related cancer such as leukemias, such as adult acute lymphoblastic leukemia, childhood acute lymphoblastic leukemia, adult acute myeloid leukemia, childhood acute myeloid leukemia, chronic lymphocytic leukemia, chronic myelogenous leukemia and hairy cell leukemia; and lymphomas, such as AIDS-related lymphoma, cutaneous T-cell lymphoma, adult Hodgkin's lymphoma, childhood Hodgkin's lymphoma, Hodgkin's lymphoma during pregnancy, mycosis fungoides, adult non-Hodgkin's lymphoma, childhood non-Hodgkin's lymphoma, non-Hodgkin's lymphoma during pregnancy, primary central nervous system lymphoma, Sezary syndrome, cutaneous T-cell lymphoma and Waldenstrom's macroglobulinemia and other hematologic/blood related cancer such as chronic myeloproliferative disorders, multiple myeloma/plasma cell neoplasm, myelodysplastic syndromes and myelodysplastic/myeloproliferative diseases;

musculoskeletal related cancer such as Ewing's family of tumours, osteosarcoma, malignant fibrous histiocytoma of bone, childhood rhabdomyosarcoma, adult soft tissue sarcoma, childhood soft tissue sarcoma and uterine sarcoma; hemangio sarcomas and angiosarcoma;

neurologic related cancer such as adult brain tumour, childhood brain tumour, brain stem glioma, cerebellar astrocytoma, cerebral astrocytoma/malignant glioma, ependmoma, medulloblastoma, supratentorial primitive neuroectodermal tumours, visual pathway and hypothalamic glioma and other brain tumours such as neuroblastoma, pituitary tumour and primary central nervous system lymphoma;

respiratory/thoracic related cancer such as non-small cell lung cancer, small cell lung cancer, malignant mesothelioma, thymoma and thymic carcinoma;

skin related cancer such as cutaneous T-cell lymphoma, Kaposi's sarcoma, melanoma, Merkel cell carcinoma and skin cancer.

In particular, the anti-IGF antibody molecules of the invention and pharmaceutical compositions containing them are beneficial in the treatment of cancers of the hematopoietic system including leukemias, lymphomas and myelomas, cancers of the gastrointestinal tract including esophageal, gastric, colorectal, pancreatic, liver and gall bladder and bile duct cancer; kidney, prostate and bladder cancer; gynecological cancers including breast, ovarian, cervical and endometrial cancer; skin and head and neck cancers including malignant melanomas; pediatric cancers like Wilms' tumour, neuroblastoma and Ewing sarcoma; brain cancers like glioblastoma; sarcomas like osteosarcoma, soft tissue sarcoma, rhabdomyosarcoma, hemangiosarcoma; lung cancer, mesothelioma and thyroid cancer.

In another embodiment, the anti-IGF antibody molecules and pharmaceutical compositions containing them are useful for non-cancerous hyperproliferative disorders such as, without limitation, psoriasis and restenosis after angioplasty. In addition, based on the recent observation (Reinberg, 2008) that a gene mutation that decreases the activity of IGF-1 has a positive effect on longevity, the antibodies of the invention have the potential to be useful, when applied to adults, in therapies to slow aging and prevent age-related diseases.

Depending on the disorder to be treated, the anti-IGF antibody molecule of the invention may be used on its own or in combination with one or more additional therapeutic agents, in particular selected from DNA damaging agents or therapeutically active compounds that inhibit angiogenesis, signal transduction pathways or mitotic checkpoints in cancer cells.

The additional therapeutic agent may be administered simultaneously with, optionally as a component of the same pharmaceutical preparation, or before or after administration of the anti-IGF antibody molecule.

In certain embodiments, the additional therapeutic agent may be, without limitation, one or more inhibitors selected from the group of inhibitors of EGFR, VEGFR, HER2-neu, AuroraA, AuroraB, PLK and PI3 kinase, FGFR, PDGFR, Raf, KSP or PDK1.

Further examples of additional therapeutic agents are inhibitors of CDK, Akt, src/bcr-abl, cKit, cMet/HGF, c-Myc, Flt3, HSP90, hedgehog antagonists, inhibitors of JAK/STAT, Mek, mTor, NFkappaB, the proteasome, Rho, an inhibitor of wnt signaling or an ubiquitination pathway inhibitor.

Examples for Aurora inhibitors are, without limitation, PHA-739358, AZD-1152, AT-9283, CYC-116, R-763, VX-667, MLN-8045, PF-3814735, SNS-314, VX-689, GSK-1070916, TTP-607, PHA-680626, MLN-8237 and ENMD-2076.

An example for a PLK inhibitor is GSK-461364.

Examples for raf inhibitors are BAY-73-4506 (also a VEGFR inhibitor), PLX-4032, RAF-265 (also a VEGFR inhibitor), sorafenib (also a VEGFR inhibitor), XL-281, and Nevavar (also an inhibitor of the VEGFR).

Examples for KSP inhibitors are ispinesib, ARRY-520, AZD-4877, CK-1122697, GSK-246053A, GSK-923295, MK-0731, SB-743921, LY-2523355, and EMD-534085.

Examples for a src and/or bcr-abl inhibitors are dasatinib, AZD-0530, bosutinib, XL-228 (also an IGF-1R inhibitor), nilotinib (also a PDGFR and cKit inhibitor), imatinib (also a cKit inhibitor), NS-187, KX2-391, AP-24534 (also an inhibitor of EGFR, FGFR, Tie2, Flt3), KM-80 and LS-104 (also an inhibitor of Flt3, Jak2).

An example for a PDK1 inhibitor is AR-12.

An example for a Rho inhibitor is BA-210.

Examples for PI3 kinase inhibitors are PX-866, PX-867, BEZ-235 (also an mTor inhibitor), XL-147, and XL-765 (also an mTor inhibitor), BGT-226, CDC-0941.

Examples for inhibitors of cMet or HGF are XL-184 (also an inhibitor of VEGFR, cKit, Flt3), PF-2341066, MK-2461, XL-880 (also an inhibitor of VEGFR), MGCD-265 (also an inhibitor of VEGFR, Ron, Tie2), SU-11274, PHA-665752, AMG-102, AV-299, ARQ-197, MetMAb, CGEN-241, BMS-777607, JNJ-38877605, PF-4217903, SGX-126, CEP-17940, AMG-458, NCB-028060, and E-7050.

An example for a c-Myc inhibitor is CX-3543.

Examples for Flt3 inhibitors are AC-220 (also an inhibitor of cKit and PDGFR), KW-2449, LS-104 (also an inhibitor of bcr-abl and Jak2), MC-2002, SB-1317, lestaurtinib (also an inhibitor of VEGFR, PDGFR, PKC), TG-101348 (also an inhibitor of JAK2), XL-999 (also an inhibitor of cKit, FGFR, PDGFR and VEGFR), sunitinib (also an inhibitor of PDGFR, VEGFR and cKit), and tandutinib (also an inhibitor of PDGFR, and cKit).

Examples for HSP90 inhibitors are, tanespimycin, alvespimycin, IPI-504, STA-9090, MEDI-561, AUY-922, CNF-2024, and SNX-5422.

Examples for JAK/STAT inhibitors are CYT-997 (also interacting with tubulin), TG-101348 (also an inhibitor of Flt3), and XL-019.

Examples for Mek inhibitors are ARRY-142886, AS-703026, PD-325901, AZD-8330, ARRY-704, RDEA-119, and XL-518.

Examples for mTor inhibitors are temsirolimus, deforolimus (which also acts as a VEGF inhibitor), everolimus (a VEGF inhibitor in addition). XL-765 (also a PI3 kinase inhibitor), and BEZ-235 (also a PI3 kinase inhibitor).

Examples for Akt inhibitors are perifosine, GSK-690693, RX-0201, and triciribine.

Examples for cKit inhibitors are masitinib, OSI-930 (also acts as a VEGFR inhibitor), AC-220 (also an inhibitor of Flt3 and PDGFR), tandutinib (also an inhibitor of Flt3 and PDGFR), axitinib (also an inhibitor of VEGFR and PDGFR), sunitinib (also an inhibitor of Flt3, PDGFR, VEGFR), and XL-820 (also acts as a VEGFR— and PDGFR inhibitor), imatinib (also a bcr-abl inhibitor), nilotinib (also an inhibitor of bcr-abl and PDGFR).

Examples for hedgehog antagonists are IPI-609, CUR-61414, GDC-0449, IPI-926, and XL-139.

Examples for CDK inhibitors are seliciclib, AT-7519, P-276, ZK-CDK (also inhibiting VEGFR2 and PDGFR), PD-332991, R-547, SNS-032, PHA-690509, PHA-848125, and SCH-727965.

Examples for proteasome inhibitors/NFkappaB pathway inhibitors are bortezomib, carfilzomib, NPI-0052, CEP-18770, MLN-2238, PR-047, PR-957, AVE-8680, and SPC-839.

An example for an ubiquitination pathway inhibitor is HBX-41108.

Examples for anti-angiogenic agents are inhibitors of the FGFR, PDGFR and VEGF(R), and thalidomides, such agents being selected from, without limitation, bevacizumab, motesanib, CDP-791, SU-14813, telatinib, KRN-951, ZK-CDK (also an inhibitor of CDK), ABT-869, BMS-690514, RAF-265, IMC-KDR, IMC-18F1, IMiDs, thalidomide, CC-4047, lenalidomide, ENMD-0995, IMC-D11, Ki-23057, brivanib, cediranib, 1B3, CP-868596, IMC-3G3, R-1530 (also an inhibitor of Flt3), sunitinib (also an inhibitor of cKit and Flt3), axitinib (also an inhibitor of cKit), lestaurtinib (also an inhibitor of Flt3 and PKC), vatalanib, tandutinib (also an inhibitor of Flt3 and cKit), pazopanib, PF-337210, aflibercept, E-7080, CHIR-258, sorafenib tosylate (also an inhibitor of Raf), vandetanib, CP-547632, OSI-930, AEE-788 (also an inhibitor of EGFR and Her2), BAY-57-9352 (also an inhibitor of Raf), BAY-73-4506 (also an inhibitor of Raf), XL-880 (also an inhibitor of cMet), XL-647 (also an inhibitor of EGFR and EphB4), XL-820 (also an inhibitor of cKit), nilotinib (also an inhibitor of cKit and brc-abl), CYT-116, PTC-299, BMS-584622, CEP-11981, dovitinib, CY-2401401, and ENMD-2976.

The additional therapeutic agent may also be selected from EGFR inhibitors, it may be a small molecule EGFR inhibitor or an anti-EGFR antibody. Examples for anti-EGFR antibodies, without limitation, are cetuximab, panitumumab, nimotuzumab, zalutumumab; examples for small molecule EGFR inhibitors are gefitinib, erlotinib and vandetanib (also an inhibitor of the VEGFR). Another example for an EGFR modulator is the EGF fusion toxin.

Further EGFR and/or Her2 inhibitors useful for combination with an anti-IGF antibody molecule of the invention are lapatinib, trastuzumab, pertuzumab, XL-647, neratinib, BMS-599626 ARRY-334543, AV-412, mAB-806, BMS-690514, JNJ-26483327, AEE-788 (also an inhibitor of VEGFR), AZD-8931, ARRY-380 ARRY-333786, IMC-11F8, Zemab, TAK-285, AZD-4769.

Other agents that may be advantageously combined in a therapy with the anti-IGF antibody molecule of the invention are tositumumab and ibritumomab tiuxetan (two radiolabelled anti-CD20 antibodies); ofatumumab, rituximab, LY-2469298, ocrelizumab, TRU-015, PRO-131921, FBT-A05, veltuzumab, R-7159 (CD20 inhibitors), alemtuzumab (an anti-CD52 antibody), denosumab, (an osteoclast differentiation factor ligand inhibitor), galiximab (a CD80 antagonist), zanolimumab (a CD4 antagonist), SGN40 (a CD40 ligand receptor modulator), XmAb-5485, Chi Lob 7/4, lucatumumab, CP-870893 (CD40 inhibitors), CAT-8015, epratuzumab, Y90-epratuzumab, inotuzumab ozogamicin (CD22 inhibitors), lumiliximab (a CD23 inhibitor), TRU-016 (a CD37 inhibitor), MDX-1342, SAR-3419, MT-103 (CD19 inhibitors), or mapatumumab, tigatuzumab, lexatumumab, Apomab, AMG-951 and AMG-655 (TRAIL receptor modulators).

Other chemotherapeutic drugs that may be used in combination with the anti-IGF antibody molecules of the present invention are selected from, but not limited to hormones, hormonal analogues and antihormonals (e.g. tamoxifen, toremifene, raloxifene, fulvestrant, megestrol acetate, flutamide, nilutamide, bicalutamide, cyproterone acetate, finasteride, buserelin acetate, fludrocortinsone, fluoxymesterone, medroxyprogesterone, octreotide, arzoxifene, pasireotide, vapreotide), aromatase inhibitors (e.g. anastrozole, letrozole, liarozole, exemestane, atamestane, formestane), LHRH agonists and antagonists (e.g. goserelin acetate, leuprolide, abarelix, cetrorelix, deslorelin, histrelin, triptorelin), antimetabolites (e.g. antifolates like methotrexate, pemetrexed, pyrimidine analogues like 5-fluorouracil, capecitabine, decitabine, nelarabine, and gemcitabine, purine and adenosine analogues such as mercaptopurine thioguanine, cladribine and pentostatin, cytarabine, fludarabine); antitumour antibiotics (e.g. anthracyclines like doxorubicin, daunorubicin, epirubicin and idarubicin, mitomycin-C, bleomycin dactinomycin, plicamycin, mitoxantrone, pixantrone, streptozocin); platinum derivatives (e.g. cisplatin, oxaliplatin, carboplatin, lobaplatin, satraplatin); alkylating agents (e.g. estramustine, meclorethamine, melphalan, chlorambucil, busulphan, dacarbazine, cyclophosphamide, ifosfamide, hydroxyurea, temozolomide, nitrosoureas such as carmustine and lomustine, thiotepa); antimitotic agents (e.g. vinca alkaloids like vinblastine, vindesine, vinorelbine, vinflunine and vincristine; and taxanes like paclitaxel, docetaxel and their formulations, larotaxel; simotaxel, and epothilones like ixabepilone, patupilone, ZK-EPO); topoisomerase inhibitors (e.g. epipodophyllotoxins like etoposide and etopophos, teniposide, amsacrine, topotecan, irinotecan) and miscellaneous chemotherapeutics such as amifostine, anagrelide, interferone alpha, procarbazine, mitotane, and porfimer, bexarotene, celecoxib.

The anti-IGF antibody molecules of the invention, e.g. when used at lower concentrations, may also be combined with agents that target the IGF-1R. Such agents include antibodies that bind to IGF-1R (e.g. CP-751871, AMG-479, IMC-A12, MK-0646, AVE-1642, R-1507, BIIB-022, SCH-717454, rhu Mab IGFR and novel chemical entities that target the kinase domain of the IGF1-R (e.g. OSI-906 or BMS-554417, XL-228, BMS-754807).

The anti-IGF antibody molecule of the invention may also be used in combination with other therapies including surgery, radiotherapy, endocrine therapy, biologic response modifiers, hyperthermia and cryotherapy and agents to attenuate any adverse effect (e.g. antiemetics).

The anti-IGF antibody molecule of the invention is also useful in diagnosis of cancers where elevated serum levels of IGF-1 and/or IGF-2 correlate with development or progression of disease, e.g. for determining elevated IGF-2 levels due to loss of imprinting (LOI), an epigenetic alteration affecting the insulin-like growth factor II gene (IGF2). In certain embodiments, an antibody for diagnostic applications, e.g. for detection of IGF-1 in human tissue sections by immunohistological staining, is a chimeric antibody that is derived from a human antibody. In such antibody, the constant regions, or parts thereof, have been replaced by the respective sequences from an antibody of another species, e.g. mouse. By using such chimeric antibody as a primary antibody, the secondary antibody, e.g. a goat antibody which specifically reacts with the murine Fc portion, will specifically recognize the murine sequences of the chimeric primary antibody and not bind to the Fc portions of the other human immunoglobulin molecules that are present in the human tissue sample. Thus, undesired background staining is avoided.

Materials & Methods

Selection of IGF-1 Binding Antibodies (Fab Fragments Comprised of the Antibody Light Chain and the Heavy Chain Variable Region with Constant Region Domain CH1) by Phage Display Selection of specific phage clones (panning) from the combinatorial HuCAL Gold library (Knappik et al., 2000) is performed essentially as described by Rauchenberger et al. (2003) in three panning cycles. Phagemid rescue, phage amplification and Fab purification are performed as described by Krebs et al. (2001). Phagemid DNA from the pool of clones from the $2^{nd}$ and $3^{rd}$ panning round is prepared with a commercially available plasmid kit (Qiaprep spin miniprep kit; Qiagen) and the Fab fragments isolated and cloned into the expression vector pMORPH9_FH (EP 859841) and transformed into E. coli TG1 F⁻. The obtained clones are transferred into 384-well microtiter masterplates (Nunc) and cultivated. Replica plates for expression are inoculated and the E. coli Fab clones induced with 0.5 mM IPTG and grown overnight at 22° C. Fab fragment-containing lysates for screening are generated by adding 15 µl BEL lysate buffer (2BBS/EDTA/Lysozyme) to 65 µl E. coli culture. After 1.5 hr, 15 µl blocking buffer (1.5% BSA/TBS or 12.5% milk powder in PBS/Tween-20) is added and incubated for 30 minutes further at 22° C. and 400 rpm.

ELISA screening for IGF-1 positive Fab clones is performed by coating Maxisorb 384-well plates overnight at 4° C. with 5 µg/ml recombinant human IGF-1 (Gropep) in 1× coating buffer (Gibco). Wells are washed with 1×TBS-T and blocked with 1× Blocking Buffer (Gibco) for 1 h at room temperature. Bacterial lysates containing antibody Fab fragments are added for 1.5 hr at room temperature, then washed five times with 1×TBS-T and detected with Alkaline Phosphatase-conjugated Affini Pure Goat Anti-HumanIgG F(ab')₂ Fragment Specific Mab (Dianova) at a dilution of 1:10 000 and visualized with Attophos Substrate (Roche). Fluorescence readings are performed on Tecan fluorescence reader at excitation 430 nm and emission 535 nm.

Cross-reactivity to recombinant human IGF-1, murine IGF-1, murine IGF-2 (R&D Systems), recombinant human IGF-2, rat IGF-1, rat IGF-2 (Gropep) and recombinant human insulin (Roche) is performed by ELISA using the same procedure as above, but with a 1 µg/ml coating dilution.

Selection of Antibodies that Neutralize IGF-1 and IGF-2 Binding to IGF-1R

To identify IGF antibodies that neutralize the ability of IGF-1 and IGF-2 to bind to the IGF-1R, an ELISA is established by coating plates with 1.5 µg/ml recombinant human IGF-1R (R&D Systems) which allows the binding of biotinylated IGF-1 and biotinylated IGF-2. Bound IGF-1 or IGF-2 is detected using alkaline phosphatase-conjugated streptavidin (1:10,000 dilution) (Roche). The neutralization potency of antibody Fab fragments is measured by adding 0.1-1 µg/ml of Fab to the wells coated with IGF-1R just prior to the addition of biotinylated IGF-1 or IGF-2 ligands. Antibody Fab fragments that block the binding of biotinylated ligand are identified by a reduction in fluorometric signal.

Cloning and Recombinant Expression of IgG1 Antibodies

Variable heavy chain regions (VH) and variable light chain regions (VL) are excised from the Fab expression vectors by restriction enzyme digestion (VH digestion: MfeI-BlpI; VL-λ:EcoRV-HpaI) and ligated into compatible restriction enzyme sites of pMORPH_h_IgG1 (EcoRI-BlpI) and pMORPH_h_IgλEcoRV-HpaI). Both plasmids are pcDNA3.1 based plasmids containing the human IgG1 heavy chain and human Igλ light chain constant regions respectively. EndoFree plasmid preparations (Qiagen) are prepared and the heavy and light chain plasmids are co-transfected into HEK293 freestyle cells (Invitrogen) at a concentration of 1 mg/L of each plasmid according to the supplier's protocol. After 72 hours the supernatant is harvested and the IgG concentration determined by ELISA. Antibody is purified on a modified protein A column (GE Healthcare), eluted into a citrate buffer and then dialysed to a concentration of 2.5 mg/ml in PBS.

Surface Plasmon Resonance Analysis for Determining Affinity Constants a) Antibody Capture Method The sensor chip is coated with approximately 1000 RU of the reference antibody in flow cell 1 and approximately 1000 RU of a rabbit-anti-human Fc-gamma-specific antibody in flow cell 2 using the coupling reagents from an amine coupling kit. A target of 1000 RU is set in the surface preparation wizard of the Biacore 3000 software at a flow rate of 5 µl/min. Running buffer used is HBS-EP. The affinity measurements are made using the following parameters: 20 µl/min flow (HCB running buffer:); 25° C. detection temperature; Fc1, Fc2 flow paths; Fc1, Fc2 detection; anti-IGF-huMAb-capturing: 3 min of a 1 µg/ml solution; 5 min IGF-Ag-association; 5 min IGF-Ag-dissociation; regeneration: 30 sec pulse with 50 mM HCl. The IGF antigens are diluted to 500, 250, 125, 62.5 and 31.3 nM in running buffer (HCB) and the different antigen dilutions are run singly over Fc1 and Fc2 with random order. Blank runs using running buffer only are run in-between. A blank run curve is subtracted from each binding curve before affinity analysis. Data evaluation is performed using the BIAevaluation software (version 4.1, Biacore, Freiburg, Germany). The dissociation and association phases of the kinetics are fitted separately. For the separate fit of the $k_{diss}$ values a time-frame of the initial 200-300 seconds in the dissociation phase is used (range of steady decrease of signal). For the separate fit of the $k_{ass}$ values, initial time frames of approx 100 seconds are used (range of steady increase of signal) and for calculation the individual $k_{diss}$ values are used with the 1:1 Langmuir association model. The average values with the standard deviations of the kinetic data together with the corresponding dissociation ($K_D$) and association ($K_A$) constants are calculated.

b) IGF Coating Method

The determination of binding constants of IGF antibodies to IGF ligands when the sensor chip is coated with IGF ligands is essentially performed as described above except that the sensor chip is coated with 35.1 pg/mm$^2$ and 38.5 pg/mm$^2$ IGF-1 and IGF-2 respectively. The antibodies are then flowed over the chip at the following concentrations: 50, 25, 12.5, 6.25, 3.12 nM.

In Vitro Cell Assays for Determining Neutralization Potency

The COLO 205 colon cancer-derived cell line (ATCC # CCL-222) is plated in 96-well plates at a cell density of 1000 cells per well in serum-free RPMI medium. 10 ng/ml of either IGF-1 or IGF-2 is added in the presence or absence of a control antibody or antibodies 40183 and 40186 at concentrations of 5 and 30 μg/ml. Cells are cultured for 5 days then the cell number in each well determined using the CellTiter-Glo luminescent cell viability assay (Promega). Luminescence was recorded using a XFluor GENios Pro 4.

Ewing Sarcoma-Derived Cell Line Growth Assays

The Ewing sarcoma-derived cell lines TC-71 (ATCC #ACC516) and SK-N-MC (ATCC #HTB86) are plated in 96-well plates at a density of 1000 cells per well in DMEM medium containing 1×NEAA, 1× sodium pyruvate, 1× glutamax and 10% fetal calf serum (FCS) and incubated overnight at 37° C. and 5% CO$_2$ in a humidified atmosphere. The following day, a serial dilution of test antibody and humanized isotype control antibody (a humanized IgG1 antibody targeted to CD44-v6) are added to the cells. The typical concentrations used are 10, 3.33, 1.11, 0.37, 0.13 and 0.04 μg/ml and each dilution is performed in triplicate wells. The cells plus antibody are then incubated for 120 hours after which time the relative cell number in each well is determined using the CellTiter-Glo luminescent cell viability assay (Promega). Luminescence is recorded using a XFluor GENios Pro 4 and for data analysis the mean value from triplicate wells is taken and fitted by iterative calculations using a sigmoidal curve analysis program (Graph Pad Prism) with variable Hill slope.

Western Blot Analysis of Phosphorylated Ribosomal S6

COLO 205 cells are plated in 6-well plates in medium containing 10% serum and after two days they are harvested and re-plated in serum-free medium. The cells are then incubated with 10 ng/ml IGF-1 or IGF-2 with or without 30 μg/ml GF antibody for four hours before being lysed and the cell lysate frozen after the protein concentration had been determined using a Bradford assay. Western blotting is performed by applying 13 μg of protein lysates to an SDS PAGE gel (BioRad) and the gel blotted on a Citerian gel blotting sandwich. Western blots are incubated overnight with both a rabbit anti-β actin (control) antibody and a rabbit anti-phospho-S6 ribosomal protein (Ser235/236) antibody (Cell Signaling) at 1:1000 dilutions in 1% milk powder. Following washing in TBS an anti-rabbit IgG HRPO-conjugated secondary antibody (Amersham) is applied for 1 hour and after further washes in TBS antibody reactivity is detected by ECL and captured on Hyperfilm (Amersham).

In Vivo Xenograft Studies

Female athymic NMRI nude mice, 6-8 weeks old, are inoculated subcutaneously in the right flank with the COLO 205 human colon tumour-derived cell line (ATCC #CCL-222) (5×10$^6$ in 100 μl Ringer solution). Tumour cell growth is assessed by measuring tumour volume three times per week using calipers and the formula: π/6× larger diameter×(smaller diameter)$^2$. Treatment is administered intravenously to groups of ten mice and commenced when tumours have developed to a size of between 130 to 270 mm$^3$. The treatment schedule consists of two times weekly intravenous infusions of vehicle and antibody 40186 at a dose of 25 mg/kg for two treatment cycles. In combinations of antibody with 5FU, a dose of 50 mg/kg 5FU is administered weekly. The study is terminated when tumours reached an average size of 1500 mm$^3$. All animal experiments are performed according to the legal requirements in Austria as well as guidelines of the American Association for Laboratory Animal Science (AALAS).

Determination of the Effect on Total Murine Serum IGF-1 Levels

Single intravenous (bolus) administrations of 12.5, 25, 50 and 100 mg/kg of antibody 40186 are given to female athymic NMRI nude mice, 6-8 weeks old (n=5). 24 hours post administration a blood sample is taken, serum collected, and total murine IGF-1 levels determined using the OCTEIA rat/mouse total IGF-1 immunocytometric assay. The assay is performed according to the manufacturer's instructions, absorbance is measured at 450 nm and evaluated using the SoftMax Pro software. A standard curve is used to determine the serum concentration of total IGF-1 in ng/ml. Statistical analysis is performed using the GraphPad Prism software.

Determination of Half Life in Cynomolgus Monkeys

Single intravenous (bolus) antibody administrations of 1 and 10 mg/kg (in a formulation containing 25 mM Na citrate pH 6, 115 mM NaCl, 0.02% Polysorbate 20 (Tween)) are given to cynomolgus monkeys (n=3 for each administrated dose). 0.5, 2, 8, 24, 48, 72, 168, 336 and 504 hours after each application a blood sample is taken and the human antibody concentration in the plasma determined by ELISA.

Example 1

Selection of IGF-1 and IGF-2 Cross-Reactive Fully Human Antibodies that Neutralise IGF-1R Interaction and do not Bind Insulin Fully human antibodies that bind IGF-1 and cross-react with IGF-2 are isolated, initially as Fab molecules, from a phage displayed antibody library. In addition to human IGF-1 and IGF-2 binding, Fab antibody fragments are selected that also bind murine and rat IGF-1 and IGF-2 but not human insulin. Selected Fabs are cloned and expressed as IgG molecules (IgG1 heavy chain and human Igλ light chain constant). As shown in FIG. 1A-H antibodies 40183 and 40186 show a concentration dependent binding to human IGF-1 (1A), human IGF-2 (1B), murine IGF-1 (1C), murine IGF-2 (1D), rat IGF-1 (1E), rat IGF-2 (1F), but not to human insulin (1G) or coating plastic (1H).

Figure 2:
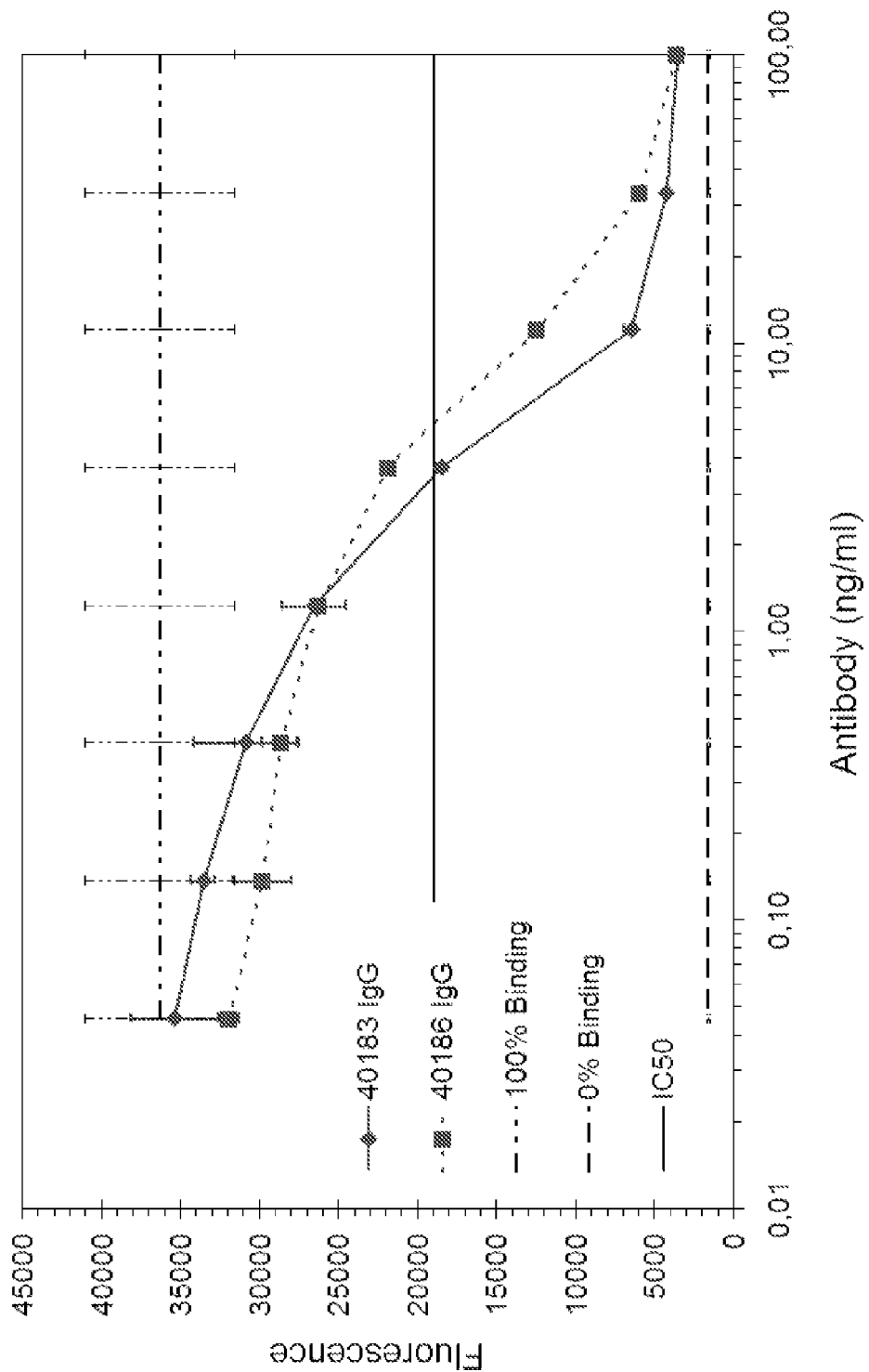
FIG. 2 shows dose-dependent neutralization of biotinylated-IGF-1 binding to coated insulin-like growth factor-1 receptor using antibodies 40183 and 40186.

Having demonstrated that antibodies 40183 and 40186 bind both IGF-1 and IGF-2, the ability of the antibodies to neutralize the interaction of IGF-1 and IGF-2 with the IGF-1R in an ELISA assay is tested. As shown in FIG. 2, both antibodies show a dose dependent inhibition of IGF-1 ligand binding with an IC$_{50}$ in this assay of approximately 5 ng/ml (0.03 nM).

Example 2

Determination of Affinity for IGF-1 and IGF-2 Using Surface Plasmon Resonance

Surface plasmon resonance is performed using a Biacore instrument to determine the affinity constants for binding of the IGF antibodies to human, rat and mouse IGF-1 and IGF-2.

Affinity (i.e. the interaction between a single antigen-binding site on an antibody and a single epitope) is expressed by the association constant $K_A=k_{ass}/k_{diss}$ or the dissociation constant $K_D=k_{diss}/k_{ass}$.

The analysis is initially performed by capturing the IGF antibodies on the sensor chip and injecting a range of antigen concentrations, thereby eliminating the possibility of an avidity effect. The resulting binding constants for antibody 40186 are listed in Table 1.

TABLE 1

BINDING CONSTANTS FOR ANTIBODY 40186 FOR HUMAN, MURINE, AND RAT IGF-1 AND IGF-2 (ANTIBODY CAPTURE METHOD)

| antigen | $k_{ass}$ [$M^{-1}s^{-1}$] | $k_{diss}$ [$s^{-1}$] | $K_A$ [$M^{-1}$] | $K_D$ [nM] |
|---|---|---|---|---|
| human IGF-1 | $5.81 * 10^5$ | $2.70 * 10^{-3}$ | $2.16 * 10^8$ | 4.66 |
| human IGF-2 | $1.03 * 10^6$ | $3.62 * 10^{-3}$ | $2.86 * 10^8$ | 3.62 |
| mouse IGF-1 | $4.66 * 10^5$ | $3.29 * 10^{-3}$ | $1.44 * 10^8$ | 7.10 |
| mouse IGF-2 | $6.32 * 10^5$ | $5.86 * 10^{-3}$ | $1.08 * 10^8$ | 9.56 |
| rat IGF-1 | $1.10 * 10^6$ | $3.01 * 10^{-3}$ | $3.67 * 10^8$ | 2.76 |
| rat IGF-2 | $6.02 * 10^5$ | $3.51 * 10^{-3}$ | $1.67 * 10^8$ | 6.49 |

Affinity constants are also determined for binding of the IGF antibodies to human IGF-1 and IGF-2 using a method where the IGF ligands are coated to the Biacore sensor chip and a range of antibody concentrations injected. The resulting binding constants for antibody 40186 using this method are listed in Table 2. The approximately 30-50-fold increase in the binding constants using this method compared with the initial antibody capture method is likely due to an avidity effect where both antibody binding domains interact with an IGF molecule.

TABLE 2

BINDING CONSTANTS FOR ANTIBODY 40186 FOR HUMAN, IGF-1 AND IGF-2 (IGF COATING METHOD)

| antigen | $k_{ass}$ [$M^{-1}s^{-1}$] | $k_{diss}$ [$s^{-1}$] | $K_A$ [$M^{-1}$] | $K_D$ [nM] |
|---|---|---|---|---|
| human IGF-1 | $2.1 * 10^6$ | $2.3 * 10^{-4}$ | $1.22 * 10^{10}$ | 0.14 |
| human IGF-2 | $2.26 * 10^6$ | $1.64 * 10^{-4}$ | $1.45 * 10^{10}$ | 0.072 |

Example 3

Effects on IGF-1 and IGF-2-Induced Cell Growth

Figure 3A:
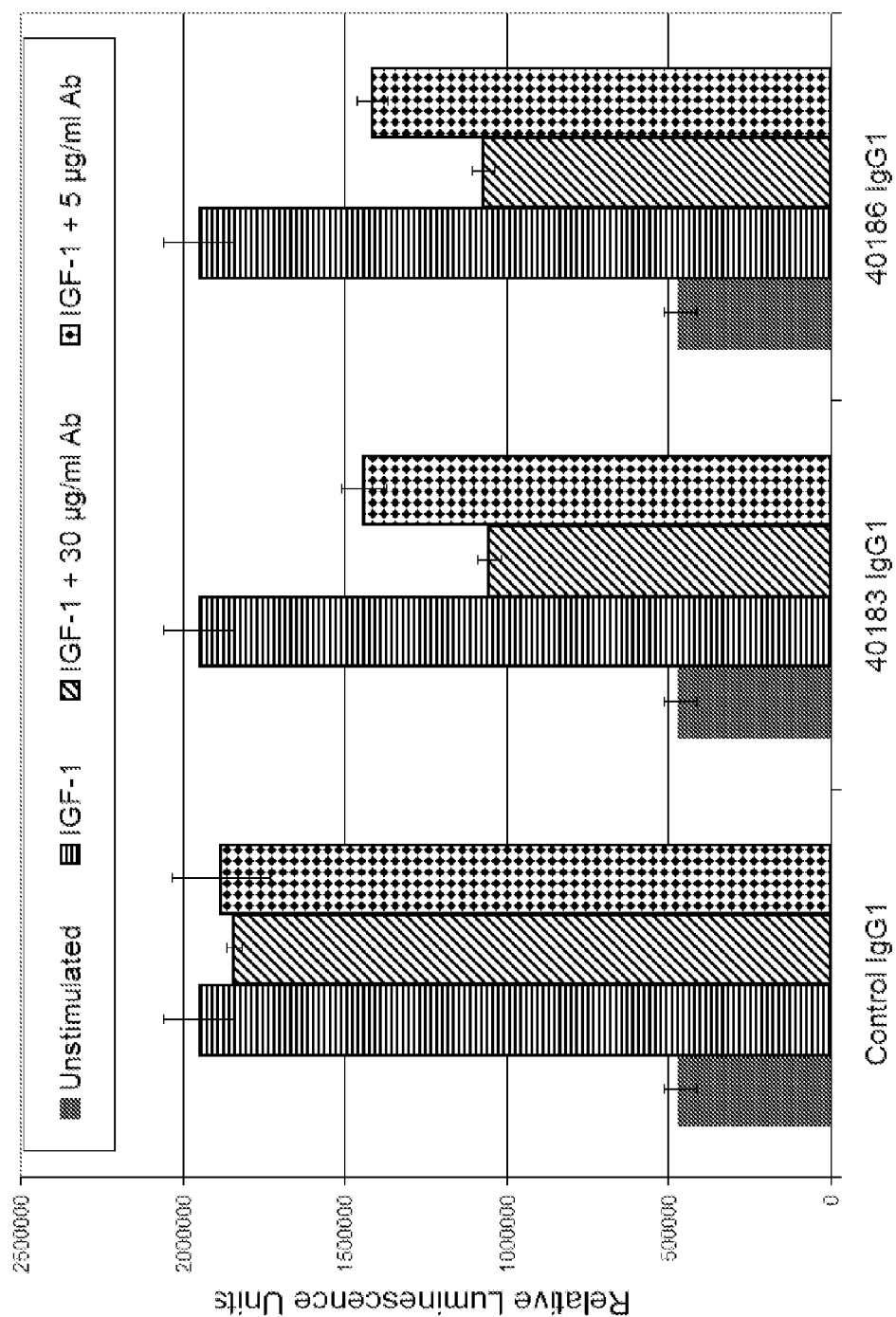
FIGS. 3A-C show the effect of antibodies 40183 and 40186 on IGF-1 (FIG. 3A), IGF-2 (FIG. 3B) and insulin (FIG. 3C) stimulated COLO 205 cell growth.
Figure 3B:
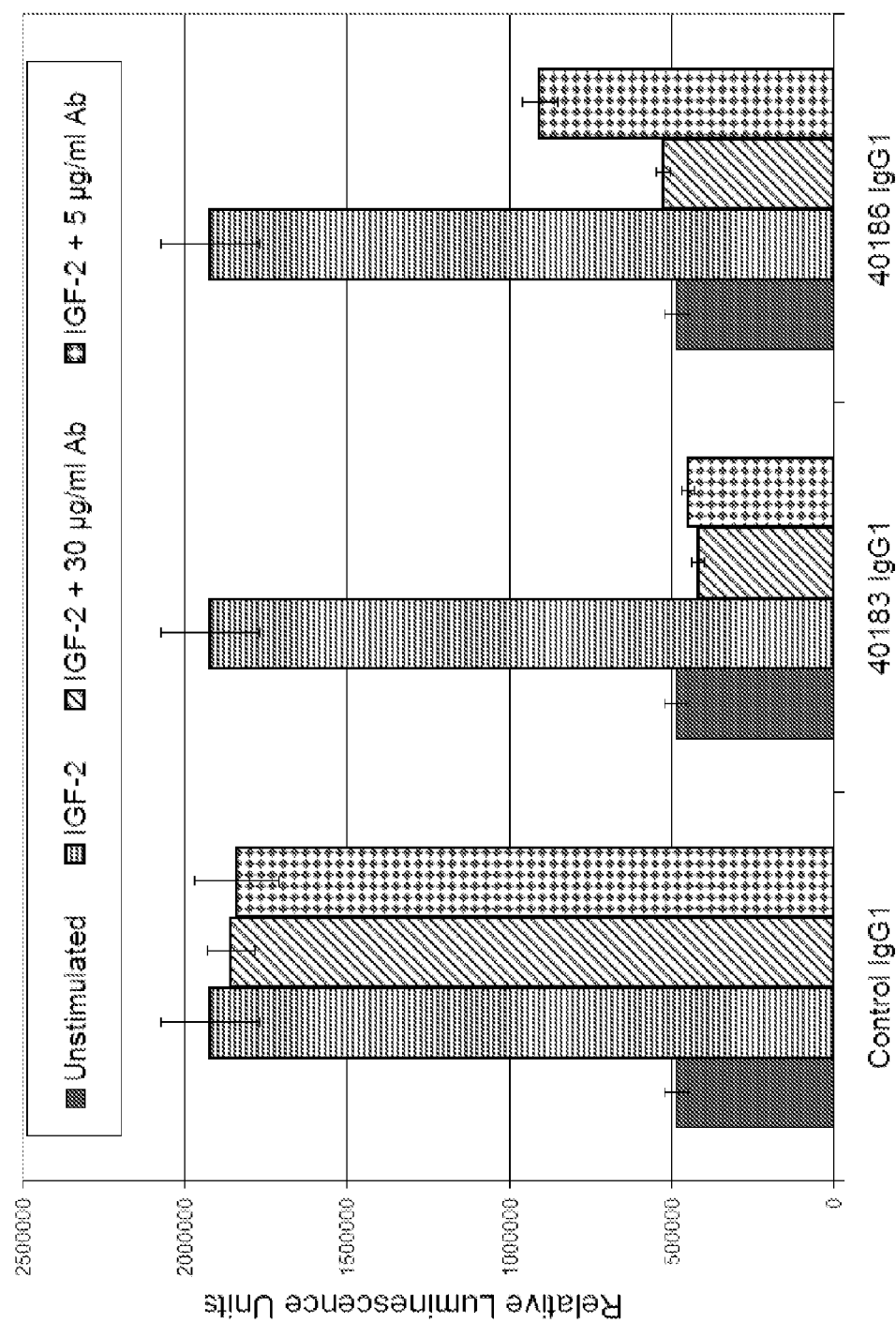
Figure 3C:
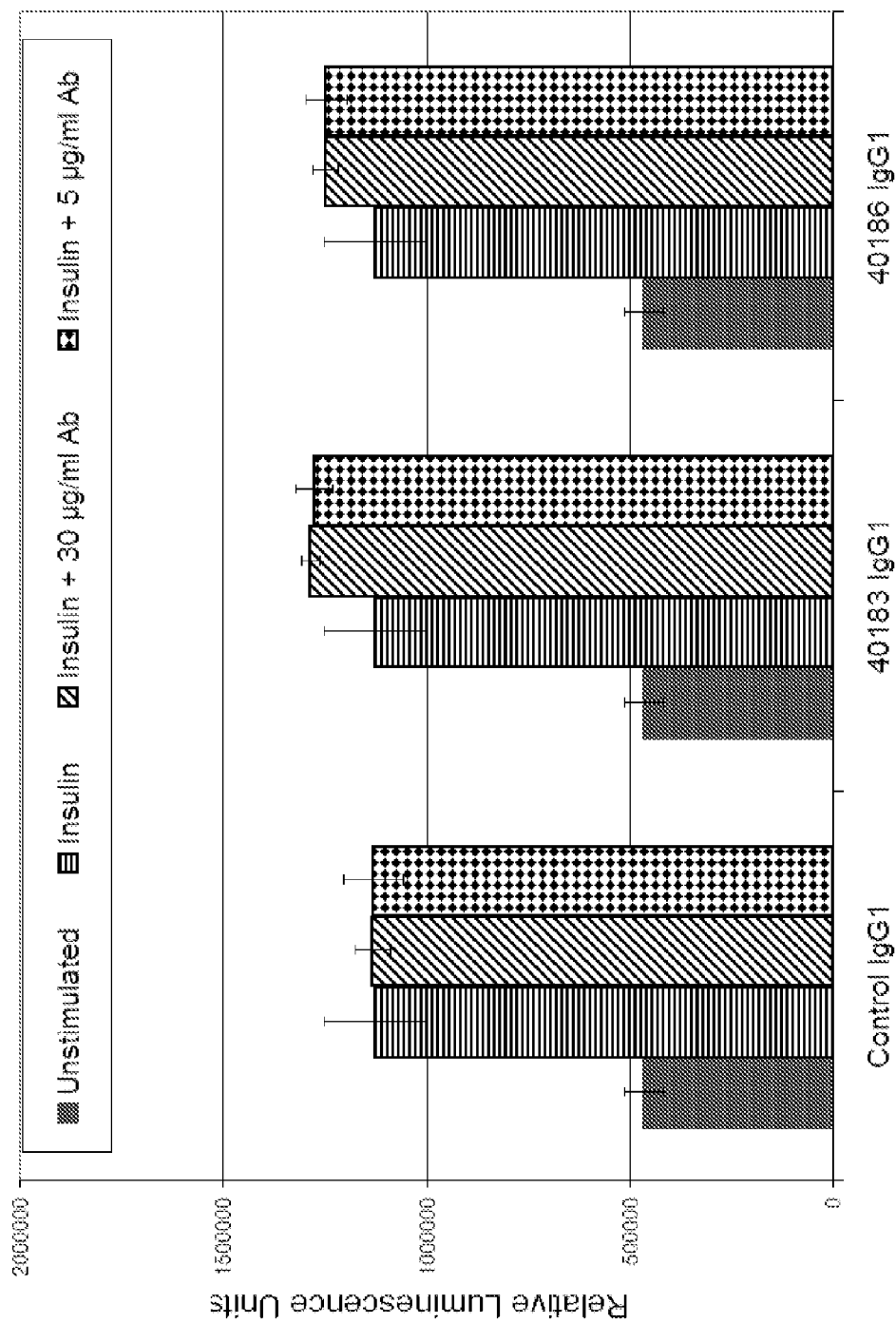

The effects of antibodies 40183 and 40186 on IGF-1, IGF-2 and insulin induced COLO 205 colon cancer cell line growth are shown in FIG. 3A-C. The antibodies show a dose dependent inhibition of IGF-1 (3A) and IGF-2 (3B) induced cell growth, but importantly have no effect on the ability of insulin to promote cell growth (3C), consistent with the finding (Example 1) that these antibodies do not bind insulin.

Figure 4:
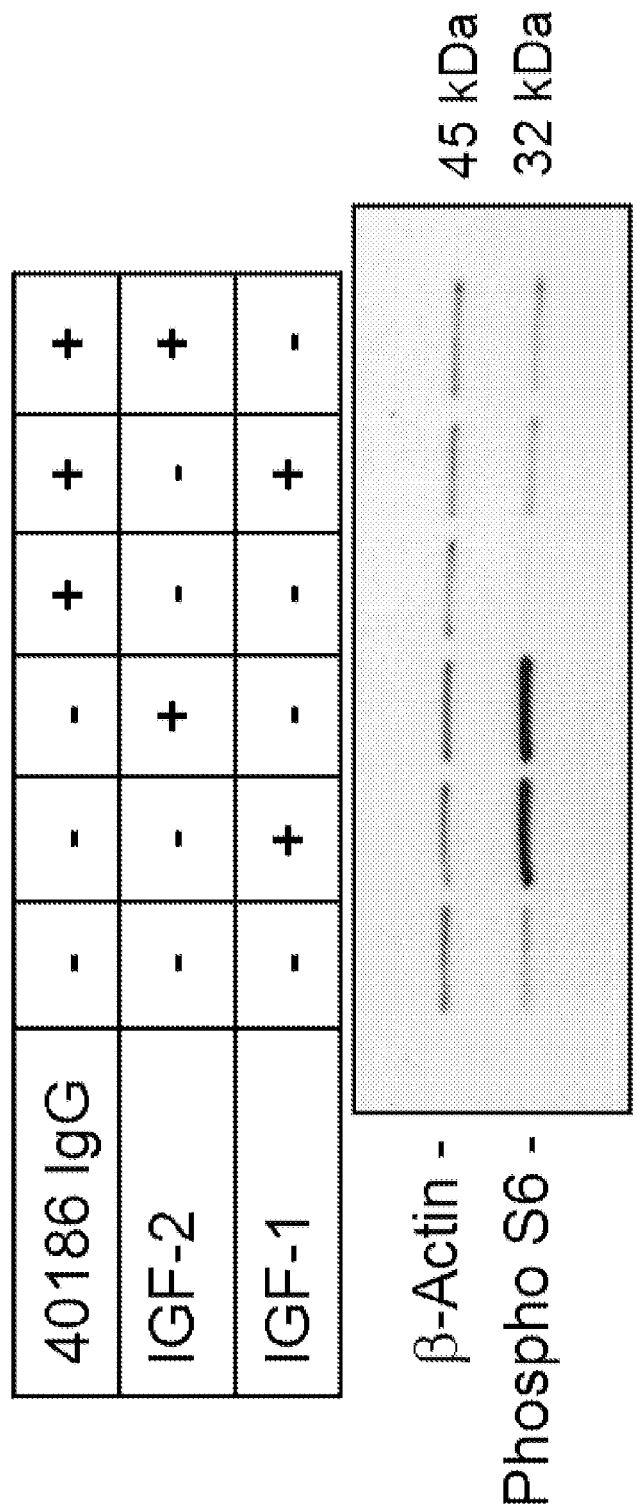
FIG. 4 shows the effect of antibody 40186 on IGF-1 and IGF-2 induced phosphorylation of ribosomal S6 protein in COLO 205 cells.

To further demonstrate that the growth inhibitory effects of the antibodies, exemplified by antibody 40186, on IGF-1 and IGF-2 induced cell growth are due to neutralization of IGFs and inhibition of the intracellular signaling pathway responsible for cell growth, the effect on ribosomal S6 protein phosphorylation is analyzed. As shown in FIG. 4, addition of either IGF-1 or IGF-2 alone results in a large increase in ribosomal S6 phosphorylation. However, addition of antibody 40186 completely neutralizes the IGF-1 and IGF-2 induced phosphorylation.

Example 4

Effects on Growth of Ewing Sarcoma-Derived Cell Lines

Figure 5A:
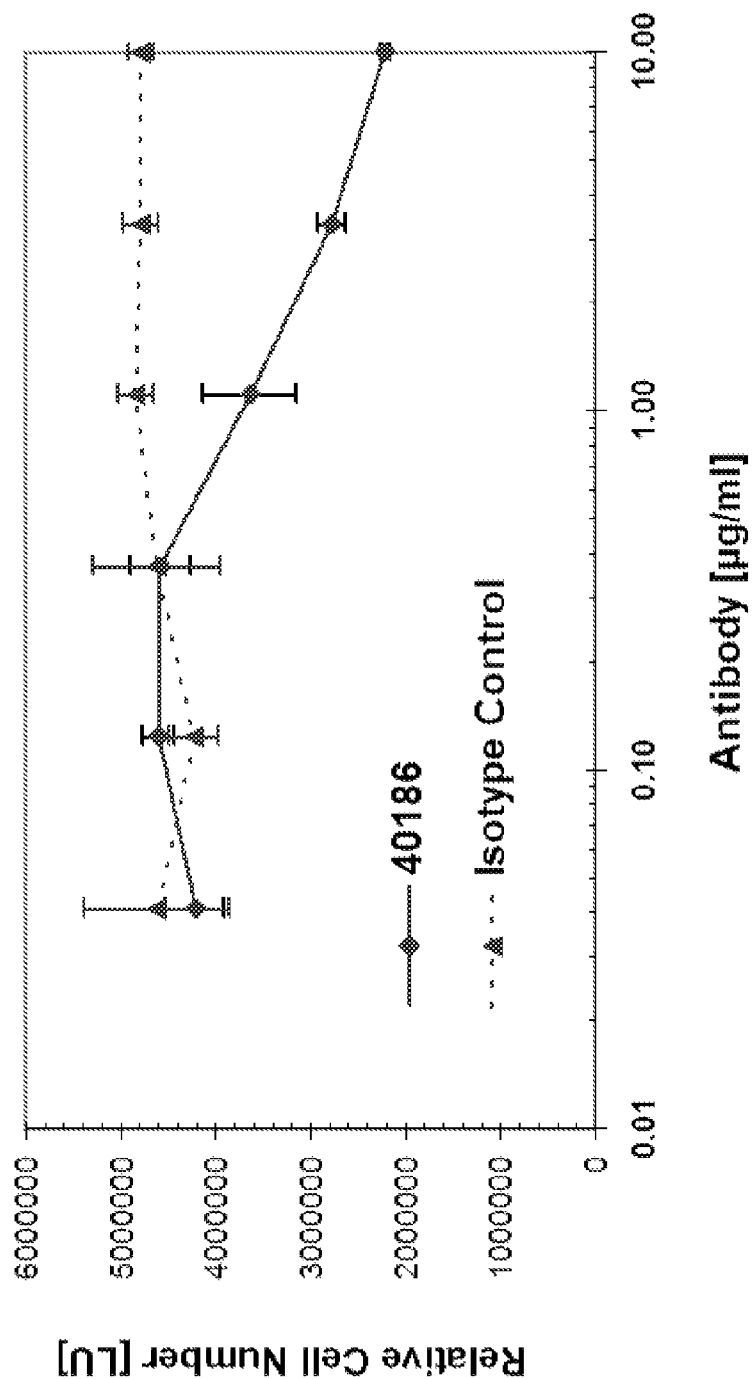
FIGS. 5 A-B show the effect of antibody 40186 on the growth of the Ewing sarcoma-derived cell lines TC-71 and SK-N-MC in 10% growth medium.
Figure 5B:
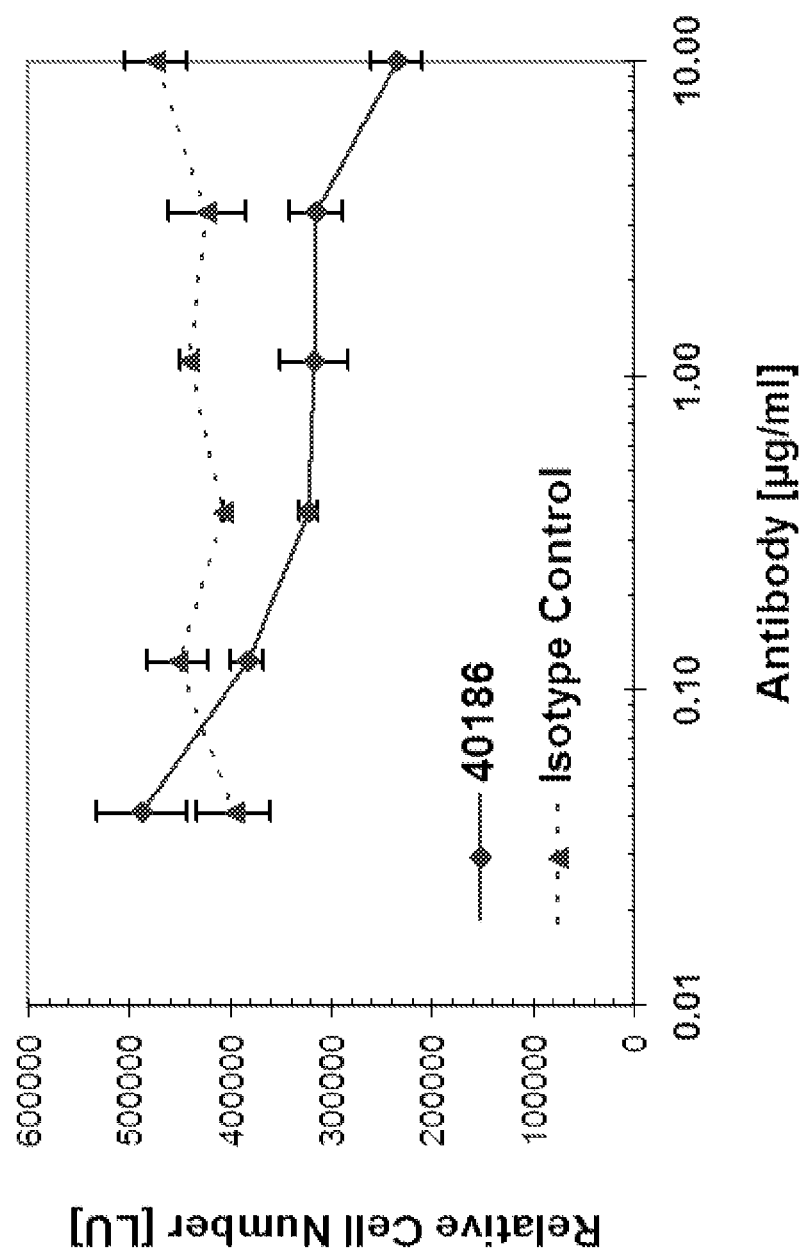

The effect of antibody 40186 on the growth of the Ewing sarcoma-derived cell lines TC-71 and SK-N-MC grown in medium containing 10% FCS is shown in FIG. 5. Relative to the humanized isotype control antibody, 40186 shows a dose-dependent inhibition of cell growth for both the TC-71 (FIG. 5A) and SK-N-MC (FIG. 5B) cell lines.

Example 5

Growth Inhibition of Colorectal Cell Tumours

Figure 6:
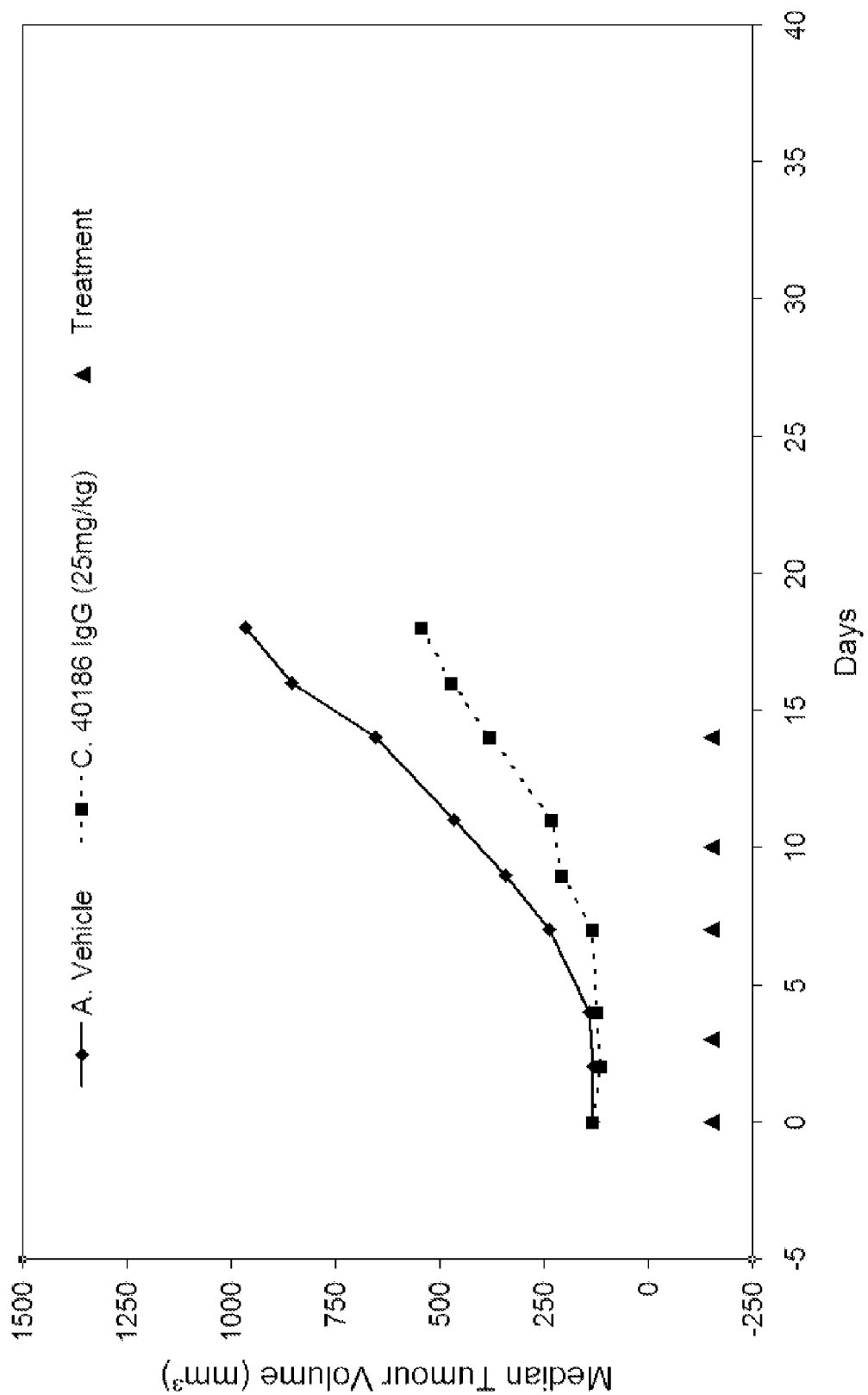
FIG. 6 shows the in vivo effect of 25 mg/kg antibody 40186 administered twice weekly on the growth of COLO 205 tumour cells xenografted into nude mice.

To demonstrate the ability of IGF-1/IGF-2 cross-reactive neutralizing antibodies to interfere with the growth of tumour cells in vivo, nude mice with established subcutaneous COLO 205 tumours are treated twice per week with 25 mg/kg antibody 40186. As shown in FIG. 6, the mice treated with 40186 show a 45% decrease in median tumour growth compared with mice treated with vehicle.

Figure 7:
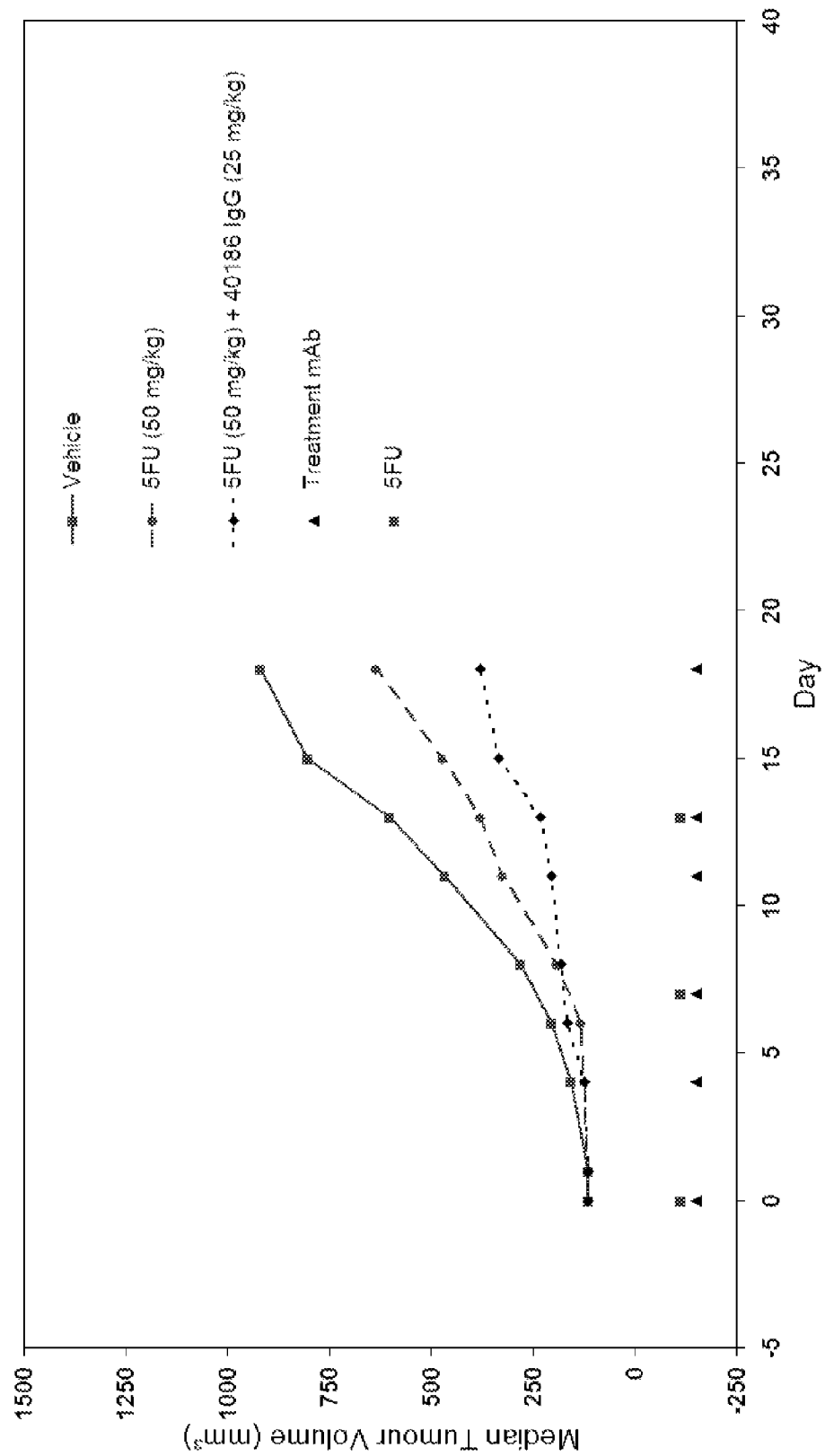
FIG. 7 shows the in vivo effect of combining 25 mg/kg antibody 40186 with 50 mg/kg 5FU on the growth of COLO 205 tumour cells xenografted into nude mice.

In addition, the effect on COLO 205 xenograft tumour growth of 25 mg/kg antibody 40186 in combination with 50 mg/kg once weekly of the cytotoxic agent 5FU was measured. As shown in FIG. 7, mice treated with a combination of 25 mg/kg 40186 antibody and 50 mg/kg 5FU show a 60% decrease in median tumour growth compared with a 30% using 50 mg/kg 5FU alone.

Example 6

Effect on Total Murine IGF-1 Levels

Figure 8:
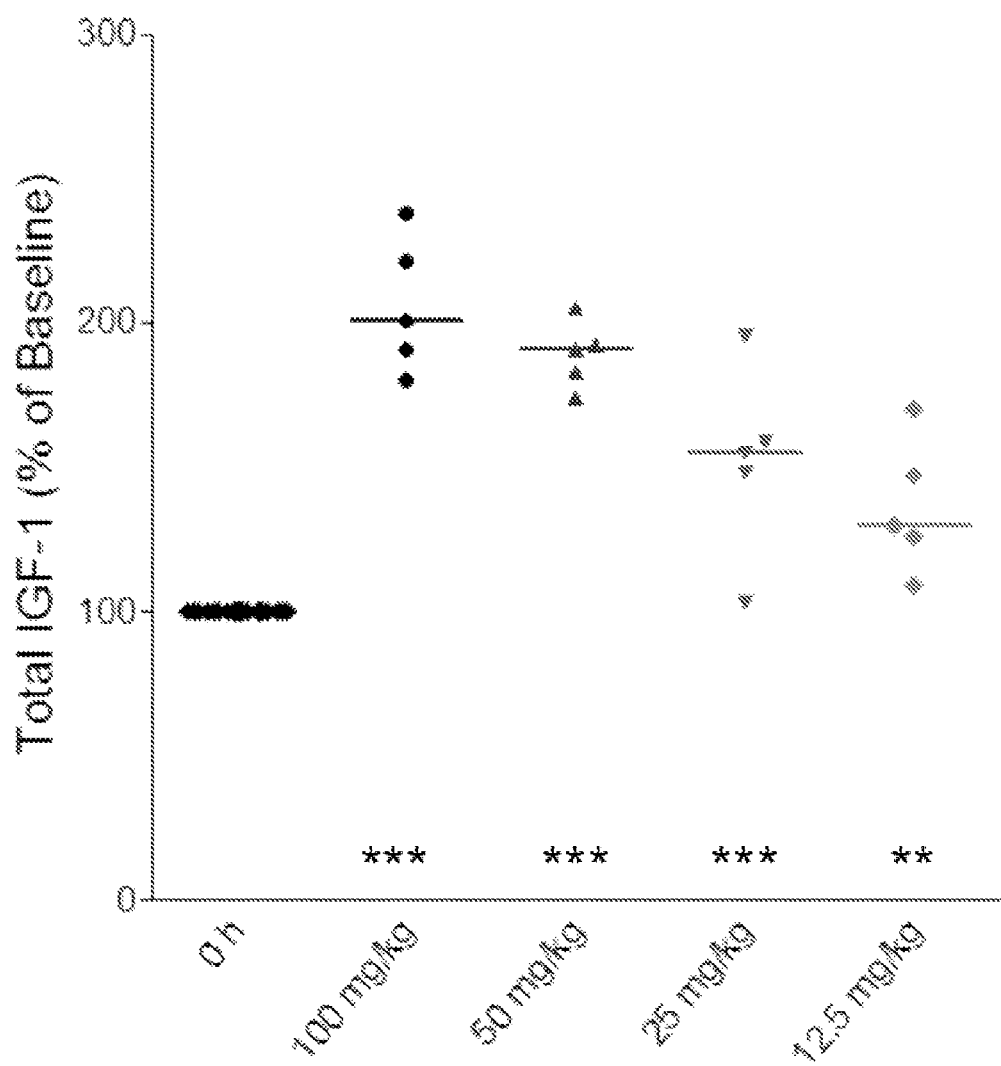
FIG. 8 shows the effect of antibody 40186 on murine total serum IGF-1 levels 24 hours following the administration of single doses of 100, 50, 25, 12.5 mg/kg.

Neutralization of active IGF-1 with an IGF targeted antibody may be expected to result in an endocrine feedback through the growth hormone pathway, which results in elevated total serum IGF-1 and IGFBP3 levels. Antibodies 40183 and 40186 are cross-reactive with mouse and rat IGF-1 which allows any pharmacodynamic effect on total serum IGF-1 levels to be measured in these species. As shown in FIG. 8, administration of antibody 40186 to athymic NMRI nude mice results in a dose dependent elevation of serum total murine IGF-1 levels 24 hour post administration. This represents a useful pharmacodynamic marker of the activity of these antibodies which can be tested during clinical development in humans.

Example 7

Terminal Half Life in Cynomolgus Monkeys

A pre-clinical estimation of the terminal half life of antibody 40186 in humans is obtained by measuring the terminal half life of 1 and 10 mg/kg single intravenous (bolus) applications in cynomolgus monkey plasma. As shown in Table 3 the half life of 40186 in cynomolgus monkeys is in the range from 10.7±1.6 days (1 mg/kg) to 12±1.4 (10 mg/kg).

TABLE 3

TERMINAL HALF LIFE OF ANTIBODY 40186
IN CYNOMOLGUS MONKEY PLASMA

| Antibody dose | Terminal Half Life (days)<br>n = 3 |
|---|---|
| 1 mg/kg | 10.7 ± 1.6 |
| 10 mg/kg | 12 ± 1.4 |

Example 8

Preparation of Production Clones

In order to prepare a clone for producing antibody 40186 or 40183, respectively, the complete heavy chain coding sequence, comprising the sequences of SEQ ID NO:13 (or SEQ ID NO:17 for 40183, respectively) and SEQ ID NO:21, is inserted into the eukaryotic expression vector pBI-26, encoding in addition the selection marker dihydrofolate reductase from hamster, resulting in the recombinant expression vector pBI-26/HC-40186 (or pBI-26/HC-40183, respectively).

The complete light chain coding sequence, comprising the sequences of SEQ ID NO:15 (or SEQ ID NO:19 for 40183, respectively) and SEQ ID NO:23, is inserted into the eukaryotic expression vector pBI-49, encoding in addition the selection marker neomycin phosphotransferase, resulting in the recombinant expression vector pBI-49/LC-40186 (or pBI-49/LC-40183, respectively. The DNA sequences of the entire heavy and light chains are sequenced completely.

The hamster cell line CHO-DG44, grown in suspension in chemically defined media, is co-transfected with the eukaryotic expression vectors for the heavy and for the light chain of the antibody 40186 (or 40183, respectively), as described above. Transfected cells are selected in medium without hypoxanthine and thymidine and in the presence of the antibiotic G418. Subsequently, cells are subjected to stepwise selection and amplification using increasing concentrations of methotrexate (MTX). From the 800 nM MTX amplification step, a single cell clone is selected based on growth performance and antibody production in spinner runs, and is cryopreserved in a Safety Cell Bank (SCB).

REFERENCES

Barbas, et al., 1994, Proc. Nat. Acad. Sci, USA 91:3809-3813.
Burtrum et al., Cancer Res. 63: 8912-21, 2003).
Chen et al., J. Clin. Endocrinol. 90: 366-371, 2005.
Chothia and Lesk, J. Mol. Biol. 196: 901-917 (1987).
Cui et al., Science 299: 1753-55, 2003.
Cruz-Correa et al., Gastroenterology 126: 1190-3, 2004.
Dufner and Thomas, Exp. Cell Res. 253: 100-109, 1999.
Frasca et al., Mol. Cell. Biol. 19: 3278-88, 1999.
Freier et al., Gut, May; 44(5): 704-08, 1999;
Fukuzawa et al., Int. J. Cancer 82: 490-497, 1999.
Goetsch et al., Int. J. Cancer 113: 316-28, 2005.
Goya et al., Cancer Res. 64: 6252-58, 2004.
Hassan et al., Cancer Res. 60: 1070-6, 2000
Hawkins et al., 1992, J. Mol. Biol. 226(3): 889 896.
Jackson et al., 1995, J. Immunol. 154(7):3310-9.
Jerome et al., End. Rel. Cancer 10: 561-578, 2003.
Kabat et al., Sequences of Proteins of Immunological Interest (5th Ed.). NIH Publication No. 91 3242. U.S. Department of Health and Human Services, Public Health Service, National Institutes of Health, Bethesda, Md. (1991).
Kipriyanow and Le Gall, Molecular Biotechnology 26: 39-60, 2004
Knappik et al., J. Mol. Biol. 296: 57-86, 2000.
Kolb et al. Pediatr. Blood Cancer 50: 1190-1197, 2008.
Krebs, B. et al., J. Immunol. Meth. 245: 67 84, 2001.
Kulik et al., Mol. Cell. Biol. 17: 1595-606, 1997.
LeRoith D, Experimental Diab. Res. 4: 205-212, 2003.
Li et al., Tumour Biol. 25: 62-8, 2004.
Lin et al., J. Pharmacol. Exp. Ther. 288: 371-378, 1999.
Lowman et al., Biochemistry 30(45): 10832-10837 (1991).
Lu JF., et al., "Clinical pharmacokinetics of bevacizumab in patients with solid tumours." Cancer Chemother. Pharmacol. 2008 Jan. 19. [Epub ahead of print]
Lund et al., Cancer Lett. 206: 85-96, 2004.
Manara et al., Clin. Cancer Res. 13: 1322-1330, 2007.
Manes et al., Endocrinology 138: 905-915, 1997
Marks et al., 1992, Biotechnology 10:779-783.
Miyamoto et al., Clin. Cancer Res. 11: 3494-3502, 2005.
Moorhead et al., Oncogene 22: 853-7, 2003.
Ng et al., J. Gastroenterol. Hepatol. 13: 152-7, 1998.
Pandini et al., J. Biol. Chem. 277: 39684-95, 2002.
Pollack et al., Nature Rev. Can. 4: 505-518, 2004.
Pollack et al., American Society for Clinical Oncology (ASCO), Annual Meeting 2007, abstract 3587.
Quinn et al., J. Biol. Chem. 271: 11477-83, 1996.
Rauchenberger, R. et al., J. Biol. Chem. 278: 38194-38205, 2003.
Reinberg, U.S, News World Report, Mar. 5, 2008.
Remington: "The Science and Practice of Pharmacy", 2005, $21^{st}$ edition, Hendrickson Randy, Editor; Advanced Concepts Institute, University of The Sciences in Philadelphia, 600 S. $43^{rd}$ Street, Philadelphia, Pa. 19104, USA; 215-895-1184.
Renehan et al., Br. J. Cancer 83: 1344-50, 2000a).
Renehan et al., J. Clin. Endocrinol. Metab. 85: 3402-8, 2000b).
Revets et al., Expert Opin Biol Ther. 5(1):111-24, 2005.
Rubin et al., Lab. Invest. 73: 311-31, 1995.
Russell et al., Proc. Natl. Acad. Sci. USA 81: 2389-2392, 1984.
Scotlandi et al., Cancer Res. 56: 4570-4574, 1996
Sell et al., Natl. Acad. Sci. USA 90: 11217-21, 1993.
Sell et al., Mol. Cell. Biol. 14: 3604-12, 1994.
Shier et al., 1995, Gene 169:147-155.
Srinivasan, M. and Roeske, R W., Curr Protein Pept Sci. 2005, Apr; 6(2):185-96.
Takanami et al., J. Surg. Oncol. 61: 205-8, 1996.
Tsai et al., Scand. J. Gastroenterol. 40: 68-75, 2005.
Wang et al., World J. Gastroenterol. 9: 267-70, 2003.
Woodson et al., J. Natl. Cancer Inst. 96: 407-10, 2004.
Yao et al., Clin. Cancer Res. 9: 2719-26, 2003a).
Yao et al., J. Clin. Invest. 111: 265-273, 2003b).
Yelton et al., 1995, Immunol. 155:1994-2004.
Zapata et al., Protein Eng. 8(10): 1057-1062., 1995.
Zhao et al., Cancer Epidemiol. Biomarkers Prev. 14: 1819-22, 2005.
WO 89/011297
WO 94/29348
WO 02/056910
WO 03/002609.
WO 03/050531
WO 03/093317
WO 04/003019
WO 04/058821
WO 2005/018671

WO 2005/027970
WO 2005/028515
WO 2007/042309
JP 2003-310275
U.S. Pat. No. 4,342,566

U.S. Pat. No. 3,773,919
U.S. Pat. No. 6,696,245
U.S. Pat. No. 6,991,790.
U.S. Pat. No. 7,060,268

The invention claimed is:

1. An isolated human antibody molecule, which binds to human IGF-1 and IGF-2, wherein said antibody molecule has:
   a) a heavy chain CDR1 comprising the amino acid sequence of SEQ ID NO:1, a heavy chain CDR2 comprising the amino acid sequence of SEQ ID NO:2, a heavy chain CDR3 comprising the amino acid sequence of SEQ ID NO:3, a light chain CDR1 comprising the amino acid sequence of SEQ ID NO:4, a light chain CDR2 comprising the amino acid sequence of SEQ ID NO:5 and a light chain CDR3 comprising the amino acid sequence of SEQ ID NO:6 or
   b) a heavy chain CDR1 comprising the amino acid sequence of SEQ ID NO:7, a heavy chain CDR2 comprising the amino acid sequence of SEQ ID NO:8, a heavy chain CDR3 comprising the amino acid sequence of SEQ ID NO:9, a light chain CDR1 comprising the amino acid sequence of SEQ ID NO:10, a light chain CDR2 comprising the amino acid sequence of SEQ ID NO:11 and a light chain CDR3 comprising the amino acid sequence of SEQ ID NO:12.

2. The antibody molecule of claim 1, which has a variable heavy chain comprising the amino acid sequence of SEQ ID NO:14.

3. The antibody molecule of claim 1, which has a variable light chain comprising the amino acid sequence of SEQ ID NO:16.

4. The antibody molecule of claim 1, which has a variable heavy chain comprising the amino acid sequence of SEQ ID NO:18.

5. The antibody molecule of claim 1, which has a variable light chain comprising the amino acid sequence of SEQ ID NO:20.

6. An antibody of claim 1, comprising a heavy chain constant region selected from the group consisting of IgG1, IgG2, IgG3, IgG4, IgM, IgA and IgE constant regions.

7. The antibody of claim 6, wherein the antibody heavy chain constant region is IgG1.

8. The antibody of claim 7, wherein said IgG1 heavy chain constant region comprises the amino acid sequence of SEQ ID NO:22.

9. An antibody of claim 1, wherein the light chain constant region is Igλ.

10. The antibody of claim 9, wherein the light chain constant region comprises the amino acid sequence of SEQ ID NO:24.

11. A human antibody molecule of claim 1, which is a Fab fragment.

12. A human antibody molecule of claim 1, which is a F(ab')$_2$ fragment.

13. A human antibody molecule of claim 1, which is a single chain Fv fragment.

14. A pharmaceutical composition comprising an antibody molecule of claim 1 and a pharmaceutically acceptable carrier.

15. The pharmaceutical composition of claim 14, further comprising one or more additional therapeutic agents selected from DNA damaging agents or one or more therapeutically active compounds that inhibit signal transduction pathways or mitotic checkpoints in cancer cells.

16. The pharmaceutical composition of claim 15, wherein said one or more therapeutically active compounds is selected from the group of inhibitors of EGFR, VEGF, HER2-neu, AuroraB, Plk1 or PI3 kinase.

17. An isolated human antibody which has
   a) a heavy chain comprising the amino acid of SEQ ID NO:25, and
   b) a light chain comprising the amino acid of SEQ ID NO:26.

* * * * *

UNITED STATES PATENT AND TRADEMARK OFFICE
CERTIFICATE OF CORRECTION

| | | |
|---|---|---|
| PATENT NO. | : 8,580,254 B2 | Page 1 of 1 |
| APPLICATION NO. | : 12/665373 | |
| DATED | : November 12, 2013 | |
| INVENTOR(S) | : Adam et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 527 days.

Signed and Sealed this
Twenty-first Day of April, 2015

Michelle K. Lee
*Director of the United States Patent and Trademark Office*

SEQUENCE LISTING

```
<160> NUMBER OF SEQ ID NOS: 26

<210> SEQ ID NO 1
<211> LENGTH: 5
<212> TYPE: PRT
<213> ORGANISM: Homo sapiens

<400> SEQUENCE: 1

Asn Tyr Trp Met His
1               5

<210> SEQ ID NO 2
<211> LENGTH: 17
<212> TYPE: PRT
<213> ORGANISM: Homo sapiens

<400> SEQUENCE: 2

Gly Ile Ser Gly Trp Ser Ser Trp Thr Tyr Tyr Ala Asp Ser Val Lys
1               5                   10                  15

Gly

<210> SEQ ID NO 3
<211> LENGTH: 13
<212> TYPE: PRT
<213> ORGANISM: Homo sapiens

<400> SEQUENCE: 3

Phe Gly Ile Asp Ala Tyr Thr Lys Val Tyr Phe Asp Tyr
1               5                   10

<210> SEQ ID NO 4
<211> LENGTH: 11
<212> TYPE: PRT
<213> ORGANISM: Homo sapiens

<400> SEQUENCE: 4

Ser Gly Asp Asn Ile Pro Leu Lys Tyr Val Ser
1               5                   10

<210> SEQ ID NO 5
<211> LENGTH: 7
<212> TYPE: PRT
<213> ORGANISM: Homo sapiens

<400> SEQUENCE: 5

Asp Asp Asn Lys Arg Pro Ser
1               5

<210> SEQ ID NO 6
<211> LENGTH: 9
<212> TYPE: PRT
<213> ORGANISM: Homo sapiens

<400> SEQUENCE: 6

Gln Ser Trp Ala Ser Thr Gly Val Val
1               5
```

```
<210> SEQ ID NO 7
<211> LENGTH: 5
<212> TYPE: PRT
<213> ORGANISM: Homo sapiens

<400> SEQUENCE: 7

Ser Phe Ala Met Ser
1               5

<210> SEQ ID NO 8
<211> LENGTH: 17
<212> TYPE: PRT
<213> ORGANISM: Homo sapiens

<400> SEQUENCE: 8

Tyr Ile Ser Tyr Leu Gly Ser Tyr Thr Gly Tyr Ala Asp Ser Val Lys
1               5                   10                  15
Gly

<210> SEQ ID NO 9
<211> LENGTH: 6
<212> TYPE: PRT
<213> ORGANISM: Homo sapiens

<400> SEQUENCE: 9

Gly Thr Lys Phe Asp Tyr
1               5

<210> SEQ ID NO 10
<211> LENGTH: 13
<212> TYPE: PRT
<213> ORGANISM: Homo sapiens

<400> SEQUENCE: 10

Thr Gly Ser Ser Ser Asn Ile Gly Thr Tyr Asp Val His
1               5                   10

<210> SEQ ID NO 11
<211> LENGTH: 7
<212> TYPE: PRT
<213> ORGANISM: Homo sapiens

<400> SEQUENCE: 11

Ser Asn Ser Lys Arg Pro Ser
1               5

<210> SEQ ID NO 12
<211> LENGTH: 5
<212> TYPE: PRT
<213> ORGANISM: Homo sapiens

<400> SEQUENCE: 12

Ser Ile Thr Arg Val
1               5

<210> SEQ ID NO 13
<211> LENGTH: 366
<212> TYPE: DNA
<213> ORGANISM: Homo sapiens
<220> FEATURE:
<221> NAME/KEY: CDS
<222> LOCATION: (1)..(366)

<400> SEQUENCE: 13 cag gtg gaa ttg gtg gaa agc ggc ggc ggc ctg gtg caa ccg ggc ggc        48
Gln Val Glu Leu Val Glu Ser Gly Gly Gly Leu Val Gln Pro Gly Gly
```

```
agc ctg cgt ctg agc tgc gcg gcc tcc gga ttt acc ttt tct aat tat      96
Ser Leu Arg Leu Ser Cys Ala Ala Ser Gly Phe Thr Phe Ser Asn Tyr
            20                  25                  30 tgg atg cat tgg gtg cgc caa gcc cct ggg aag ggt ctc gag tgg gtg     144
Trp Met His Trp Val Arg Gln Ala Pro Gly Lys Gly Leu Glu Trp Val
 35                  40                  45 agc ggt atc tct ggt tgg tct agc tgg acc tat tat gcg gat agc gtg     192
Ser Gly Ile Ser Gly Trp Ser Ser Trp Thr Tyr Tyr Ala Asp Ser Val
 50                  55                  60 aaa ggc cgt ttt acc att tca cgt gat aat tcg aaa aac acc ctg tat     240
Lys Gly Arg Phe Thr Ile Ser Arg Asp Asn Ser Lys Asn Thr Leu Tyr
65                  70                  75                  80 ctg caa atg aac agc ctg cgt gcg gaa gat acg gcc gtg tat tat tgc     288
Leu Gln Met Asn Ser Leu Arg Ala Glu Asp Thr Ala Val Tyr Tyr Cys
                85                  90                  95 gcg cgt ttt ggt att gat gct tat act aag gtt tat ttt gat tat tgg     336
Ala Arg Phe Gly Ile Asp Ala Tyr Thr Lys Val Tyr Phe Asp Tyr Trp
            100                 105                 110 ggc caa ggc acc ctg gtg acg gtt agc tca                             366
Gly Gln Gly Thr Leu Val Thr Val Ser Ser
        115                 120
```

<210> SEQ ID NO 14
<211> LENGTH: 122
<212> TYPE: PRT
<213> ORGANISM: Homo sapiens

<400> SEQUENCE: 14

```
Gln Val Glu Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met His Trp Val Arg Gln Ala Pro Gly Lys Gly Leu Glu Trp Val
         35                 40                  45

Ser Gly Ile Ser Gly Trp Ser Ser Trp Thr Tyr Tyr Ala Asp Ser Val
     50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                85                  90                  95

Ala Arg Phe Gly Ile Asp Ala Tyr Thr Lys Val Tyr Phe Asp Tyr Trp
            100                 105                 110

Gly Gln Gly Thr Leu Val Thr Val Ser Ser
        115                 120
```

<210> SEQ ID NO 15
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 15

```
gat atc gaa ctg acc cag ccg cct tca gtg agc gtt gca cca ggt cag      48
Asp Ile Glu Leu Thr Gln Pro Pro Ser Val Ser Val Ala Pro Gly Gln
1               5                   10                  15 acc gcg cgt atc tcg tgt agc ggc gat aat att cct ctt aag tat gtt      96
Thr Ala Arg Ile Ser Cys Ser Gly Asp Asn Ile Pro Leu Lys Tyr Val
            20                  25                  30
```

```
tct tgg tac cag cag aaa ccc ggg cag gcg cca gtt ctt gtg att cat    144
Ser Trp Tyr Gln Gln Lys Pro Gly Gln Ala Pro Val Leu Val Ile His
        35                  40                  45 gat gat aat aag cgt ccc tca ggc atc ccg gaa cgc ttt agc gga tcc    192
Asp Asp Asn Lys Arg Pro Ser Gly Ile Pro Glu Arg Phe Ser Gly Ser
 50                  55                  60 aac agc ggc aac acc gcg acc ctg acc att agc ggc act cag gcg gaa    240
Asn Ser Gly Asn Thr Ala Thr Leu Thr Ile Ser Gly Thr Gln Ala Glu
 65                  70                  75                  80 gac gaa gcg gat tat tat tgc cag tct tgg gct tct act ggt gtt gtg    288
Asp Glu Ala Asp Tyr Tyr Cys Gln Ser Trp Ala Ser Thr Gly Val Val
                 85                  90                  95 ttt ggc ggc ggc acg aag tta acc gtc cta ggt                        321
Phe Gly Gly Gly Thr Lys Leu Thr Val Leu Gly
            100                 105

<210> SEQ ID NO 16
<211> LENGTH: 107
<212> TYPE: PRT
<213> ORGANISM: Homo sapiens

<400> SEQUENCE: 16

Asp Ile Glu Leu Thr Gln Pro Pro Ser Val Ser Val Ala Pro Gly Gln
 1               5                   10                  15

Thr Ala Arg Ile Ser Cys Ser Gly Asp Asn Ile Pro Leu Lys Tyr Val
            20                  25                  30

Ser Trp Tyr Gln Gln Lys Pro Gly Gln Ala Pro Val Leu Val Ile His
        35                  40                  45

Asp Asp Asn Lys Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gln Ser Trp Ala Ser Thr Gly Val Val
                 85                  90                  95

Phe Gly Gly Gly Thr Lys Leu Thr Val Leu Gly
            100                 105

<210> SEQ ID NO 17
<211> LENGTH: 345
<212> TYPE: DNA
<213> ORGANISM: Homo sapiens
<220> FEATURE:
<221> NAME/KEY: CDS
<222> LOCATION: (1)..(345)

<400> SEQUENCE: 17 cag gtg gaa ttg gtg gaa agc ggc ggc ggc ctg gtg caa ccg ggc ggc     48
Gln Val Glu Leu Val Glu Ser Gly Gly Gly Leu Val Gln Pro Gly Gly
 1               5                   10                  15 agc ctg cgt ctg agc tgc gcg gcc tcc gga ttt acc tgg tct tct ttt     96
Ser Leu Arg Leu Ser Cys Ala Ala Ser Gly Phe Thr Trp Ser Ser Phe
            20                  25                  30 gct atg tct tgg gtg cgc caa gcc cct ggg aag ggt ctc gag tgg gtg    144
Ala Met Ser Trp Val Arg Gln Ala Pro Gly Lys Gly Leu Glu Trp Val
        35                  40                  45 agc tat atc tct tat ctt ggt agc tat acc ggt tat gcg gat agc gtg    192
Ser Tyr Ile Ser Tyr Leu Gly Ser Tyr Thr Gly Tyr Ala Asp Ser Val
 50                  55                  60 aaa ggc cgt ttt acc att tca cgt gat aat tcg aaa aac acc ctg tat    240
Lys Gly Arg Phe Thr Ile Ser Arg Asp Asn Ser Lys Asn Thr Leu Tyr
 65                  70                  75                  80
```

```
ctg caa atg aac agc ctg cgt gcg gaa gat acg gcc gtg tat tat tgc      288
Leu Gln Met Asn Ser Leu Arg Ala Glu Asp Thr Ala Val Tyr Tyr Cys
             85                  90                  95 gcg cgt ggt act aag ttt gat tat tgg ggc caa ggc acc ctg gtg acg      336
Ala Arg Gly Thr Lys Phe Asp Tyr Trp Gly Gln Gly Thr Leu Val Thr
        100                 105                 110 gtt agc tca                                                          345
Val Ser Ser
        115

<210> SEQ ID NO 18
<211> LENGTH: 115
<212> TYPE: PRT
<213> ORGANISM: Homo sapiens

<400> SEQUENCE: 18

Gln Val Glu Leu Val Glu Ser Gly Gly Gly Leu Val Gln Pro Gly Gly
1               5                   10                  15

Ser Leu Arg Leu Ser Cys Ala Ala Ser Gly Phe Thr Trp Ser Ser Phe
            20                  25                  30

Ala Met Ser Trp Val Arg Gln Ala Pro Gly Lys Gly Leu Glu Trp Val
        35                  40                  45

Ser Tyr Ile Ser Tyr Leu Gly Ser Tyr Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Thr Lys Phe Asp Tyr Trp Gly Gln Gly Thr Leu Val Thr
            100                 105                 110

Val Ser Ser
        115

<210> SEQ ID NO 19
<211> LENGTH: 315
<212> TYPE: DNA
<213> ORGANISM: Homo sapiens
<220> FEATURE:
<221> NAME/KEY: CDS
<222> LOCATION: (1)..(315)

<400> SEQUENCE: 19 gat atc gtg ctg acc cag ccg cct tca gtg agt ggc gca cca ggt cag      48
Asp Ile Val Leu Thr Gln Pro Pro Ser Val Ser Gly Ala Pro Gly Gln
1               5                   10                  15 cgt gtg acc atc tcg tgt acg ggc agc agc agc aac att ggt act tat      96
Arg Val Thr Ile Ser Cys Thr Gly Ser Ser Ser Asn Ile Gly Thr Tyr
            20                  25                  30 gat gtg cat tgg tac cag cag ttg ccc ggg acg gcg ccg aaa ctt ctg      144
Asp Val His Trp Tyr Gln Gln Leu Pro Gly Thr Ala Pro Lys Leu Leu
        35                  40                  45 att tat tct aat tct aag cgt ccc tca ggc gtg ccg gat cgt ttt agc      192
Ile Tyr Ser Asn Ser Lys Arg Pro Ser Gly Val Pro Asp Arg Phe Ser
    50                  55                  60 gga tcc aaa agc ggc acc agc gcg agc ctt gcg att acg ggc ctg caa      240
Gly Ser Lys Ser Gly Thr Ser Ala Ser Leu Ala Ile Thr Gly Leu Gln
65                  70                  75                  80 agc gaa gac gaa gcg gat tac tat tgc tct att act cgt gtg ttt ggc      288
Ser Glu Asp Glu Ala Asp Tyr Tyr Cys Ser Ile Thr Arg Val Phe Gly
                85                  90                  95
```

```
ggc ggc acg aag tta acc gtc cta ggt                                     315
Gly Gly Thr Lys Leu Thr Val Leu Gly
            100                 105

<210> SEQ ID NO 20
<211> LENGTH: 105
<212> TYPE: PRT
<213> ORGANISM: Homo sapiens

<400> SEQUENCE: 20

Asp Ile Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Thr Tyr
            20                  25                  30

Asp Val His Trp Tyr Gln Gln Leu Pro Gly Thr Ala Pro Lys Leu Leu
        35                  40                  45

Ile Tyr Ser Asn Ser Lys Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Ser Ile Thr Arg Val Phe Gly
                85                  90                  95

Gly Gly Thr Lys Leu Thr Val Leu Gly
            100                 105

<210> SEQ ID NO 21
<211> LENGTH: 993
<212> TYPE: DNA
<213> ORGANISM: Homo sapiens
<220> FEATURE:
<221> NAME/KEY: CDS
<222> LOCATION: (1)..(993)

<400> SEQUENCE: 21 gcc tcc acc aag ggt cca tcg gtc ttc ccc ctg gca ccc tcc tcc aag        48
Ala Ser Thr Lys Gly Pro Ser Val Phe Pro Leu Ala Pro Ser Ser Lys
1               5                   10                  15 agc acc tct ggg ggc aca gcg gcc ctg ggc tgc ctg gtc aag gac tac        96
Ser Thr Ser Gly Gly Thr Ala Ala Leu Gly Cys Leu Val Lys Asp Tyr
            20                  25                  30 ttc ccc gaa ccg gtg acg gtg tcg tgg aac tca ggc gcc ctg acc agc       144
Phe Pro Glu Pro Val Thr Val Ser Trp Asn Ser Gly Ala Leu Thr Ser
        35                  40                  45 ggc gtg cac acc ttc ccg gct gtc cta cag tcc tca gga ctc tac tcc       192
Gly Val His Thr Phe Pro Ala Val Leu Gln Ser Ser Gly Leu Tyr Ser
    50                  55                  60 ctc agc agc gtg gtg acc gtg ccc tcc agc agc ttg ggc acc cag acc       240
Leu Ser Ser Val Val Thr Val Pro Ser Ser Ser Leu Gly Thr Gln Thr
65                  70                  75                  80 tac atc tgc aac gtg aat cac aag ccc agc aac acc aag gtg gac aag       288
Tyr Ile Cys Asn Val Asn His Lys Pro Ser Asn Thr Lys Val Asp Lys
                85                  90                  95 aaa gtt gag ccc aaa tct tgt gac aaa act cac aca tgc cca ccg tgc       336
Lys Val Glu Pro Lys Ser Cys Asp Lys Thr His Thr Cys Pro Pro Cys
            100                 105                 110 cca gca cct gaa ctc ctg ggg gga ccg tca gtc ttc ctc ttc ccc cca       384
Pro Ala Pro Glu Leu Leu Gly Gly Pro Ser Val Phe Leu Phe Pro Pro
        115                 120                 125 aaa ccc aag gac acc ctc atg atc tcc cgg acc cct gag gtc aca tgc       432
Lys Pro Lys Asp Thr Leu Met Ile Ser Arg Thr Pro Glu Val Thr Cys
    130                 135                 140
```

```
gtg gtg gtg gac gtg agc cac gaa gac cct gag gtc aag ttc aac tgg        480
Val Val Val Asp Val Ser His Glu Asp Pro Glu Val Lys Phe Asn Trp
145                 150                 155                 160 tac gtg gac ggc gtg gag gtg cat aat gcc aag aca aag ccg cgg gag        528
Tyr Val Asp Gly Val Glu Val His Asn Ala Lys Thr Lys Pro Arg Glu
                165                 170                 175 gag cag tac aac agc acg tac cgg gtg gtc agc gtc ctc acc gtc ctg        576
Glu Gln Tyr Asn Ser Thr Tyr Arg Val Val Ser Val Leu Thr Val Leu
            180                 185                 190 cac cag gac tgg ctg aat ggc aag gag tac aag tgc aag gtc tcc aac        624
His Gln Asp Trp Leu Asn Gly Lys Glu Tyr Lys Cys Lys Val Ser Asn
        195                 200                 205 aaa gcc ctc cca gcc ccc atc gag aaa acc atc tcc aaa gcc aaa ggg        672
Lys Ala Leu Pro Ala Pro Ile Glu Lys Thr Ile Ser Lys Ala Lys Gly
    210                 215                 220 cag ccc cga gaa cca cag gtg tac acc ctg ccc cca tcc cgg gat gag        720
Gln Pro Arg Glu Pro Gln Val Tyr Thr Leu Pro Pro Ser Arg Asp Glu
225                 230                 235                 240 ctg acc aag aac cag gtc agc ctg acc tgc ctg gtc aaa ggc ttc tat        768
Leu Thr Lys Asn Gln Val Ser Leu Thr Cys Leu Val Lys Gly Phe Tyr
                245                 250                 255 ccc agc gac atc gcc gtg gag tgg gag agc aat ggg cag ccg gag aac        816
Pro Ser Asp Ile Ala Val Glu Trp Glu Ser Asn Gly Gln Pro Glu Asn
                260                 265                 270 aac tac aag acc acg cct ccc gtg ctg gac tcc gac ggc tcc ttc ttc        864
Asn Tyr Lys Thr Thr Pro Pro Val Leu Asp Ser Asp Gly Ser Phe Phe
            275                 280                 285 ctc tac agc aag ctc acc gtg gac aag agc agg tgg cag cag ggg aac        912
Leu Tyr Ser Lys Leu Thr Val Asp Lys Ser Arg Trp Gln Gln Gly Asn
        290                 295                 300 gtc ttc tca tgc tcc gtg atg cat gag gct ctg cac aac cac tac acg        960
Val Phe Ser Cys Ser Val Met His Glu Ala Leu His Asn His Tyr Thr
305                 310                 315                 320 cag aag agc ctc tcc ctg tct ccg ggt aaa tga                            993
Gln Lys Ser Leu Ser Leu Ser Pro Gly Lys
                325                 330

<210> SEQ ID NO 22
<211> LENGTH: 330
<212> TYPE: PRT
<213> ORGANISM: Homo sapiens

<400> SEQUENCE: 22

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125
```

```
Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 23
<211> LENGTH: 318
<212> TYPE: DNA
<213> ORGANISM: Homo sapiens
<220> FEATURE:
<221> NAME/KEY: CDS
<222> LOCATION: (1)..(318)

<400> SEQUENCE: 23 cag ccc aag gct gcc ccc tcg gtc act ctg ttc ccg ccc tcc tct gag     48
Gln Pro Lys Ala Ala Pro Ser Val Thr Leu Phe Pro Pro Ser Ser Glu
1               5                   10                  15 gag ctt caa gcc aac aag gcc aca ctg gtg tgt ctc ata agt gac ttc     96
Glu Leu Gln Ala Asn Lys Ala Thr Leu Val Cys Leu Ile Ser Asp Phe
                20                  25                  30 tac ccg gga gcc gtg aca gtg gcc tgg aag gga gat agc agc ccc gtc    144
Tyr Pro Gly Ala Val Thr Val Ala Trp Lys Gly Asp Ser Ser Pro Val
            35                  40                  45 aag gcg gga gtg gag acc acc aca ccc tcc aaa caa agc aac aac aag    192
Lys Ala Gly Val Glu Thr Thr Thr Pro Ser Lys Gln Ser Asn Asn Lys
50                  55                  60 tac gcg gcc agc agc tat ctg agc ctg acg cct gag cag tgg aag tcc    240
Tyr Ala Ala Ser Ser Tyr Leu Ser Leu Thr Pro Glu Gln Trp Lys Ser
65                  70                  75                  80 cac aga agc tac agc tgc cag gtc acg cat gaa ggg agc acc gtg gag    288
His Arg Ser Tyr Ser Cys Gln Val Thr His Glu Gly Ser Thr Val Glu
                85                  90                  95 aag aca gtg gcc cct aca gaa tgt tca tag                            318
Lys Thr Val Ala Pro Thr Glu Cys Ser
            100                 105

<210> SEQ ID NO 24
```

<211> LENGTH: 105
<212> TYPE: PRT
<213> ORGANISM: Homo sapiens

<400> SEQUENCE: 24

```
Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Gly Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105
```

<210> SEQ ID NO 25
<211> LENGTH: 452
<212> TYPE: PRT
<213> ORGANISM: Homo sapiens

<400> SEQUENCE: 25

```
Gln Val Glu Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met His Trp Val Arg Gln Ala Pro Gly Lys Gly Leu Glu Trp Val
        35                  40                  45

Ser Gly Ile Ser Gly Trp Ser Trp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Gly Ile Asp Ala Tyr Thr Lys Val Tyr Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240
```

```
Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
            290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
            355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
    450

<210> SEQ ID NO 26
<211> LENGTH: 212
<212> TYPE: PRT
<213> ORGANISM: Homo sapiens

<400> SEQUENCE: 26

Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Pro Leu Lys Tyr Val
            20                  25                  30

Ser Trp Tyr Gln Gln Lys Pro Gly Gln Ala Pro Val Leu Val Ile His
            35                  40                  45

Asp Asp Asn Lys Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Glu
65              70                  75                  80

Asp Glu Ala Asp Tyr Tyr Cys Gln Ser Trp Ala Ser Thr Gly Val Val
            85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
            115                 120                 125

Lys Ala Thr Leu Val Cys Leu Ile Ser Asp Phe Tyr Pro Gly Ala Val
        130                 135                 140

Thr Val Ala Trp Lys Gly Asp Ser Ser Pro Val Lys Ala Gly Val Glu
145                 150                 155                 160
```

```
                                        -continued

Thr Thr Thr Pro Ser Lys Gln Ser Asn Asn Lys Tyr Ala Ala Ser Ser
            165                 170                 175

Tyr Leu Ser Leu Thr Pro Glu Gln Trp Lys Ser His Arg Ser Tyr Ser
            180             185                 190

Cys Gln Val Thr His Glu Gly Ser Thr Val Glu Lys Thr Val Ala Pro
        195                 200                 205

Thr Glu Cys Ser
        210
```